US009420832B2

(12) United States Patent
Arnold

(10) Patent No.: US 9,420,832 B2
(45) Date of Patent: Aug. 23, 2016

(54) PROGRESSIVE MOBILITY ASSISTANCE GARMENT FOR REHABILITATION

(71) Applicant: Jeanne Margaret Arnold, Bay City, MI (US)

(72) Inventor: Jeanne Margaret Arnold, Bay City, MI (US)

( * ) Notice: Subject to any disclaimer, the term of this patent is extended or adjusted under 35 U.S.C. 154(b) by 637 days.

(21) Appl. No.: 13/694,978

(22) Filed: Jan. 23, 2013

(65) Prior Publication Data

US 2013/0205466 A1 Aug. 15, 2013

Related U.S. Application Data

(60) Provisional application No. 61/632,886, filed on Feb. 1, 2012.

(51) Int. Cl.

| | |
|---|---|
| ***A61F 5/00*** | (2006.01) |
| ***A41D 1/00*** | (2006.01) |
| ***A61G 7/10*** | (2006.01) |

(52) U.S. Cl.

CPC ................ *A41D 1/00* (2013.01); *A61G 7/1051* (2013.01); *A61G 2200/32* (2013.01); *A61G 2200/34* (2013.01); *A61G 2200/36* (2013.01)

(58) Field of Classification Search

CPC ........... A61H 2201/163; A61H 1/0218; A61H 2201/0107; A61H 2201/0192; A61H 2201/1616; A61H 2201/1621; A61H 2201/1642; A61H 2201/1652; A61H 2203/0493; A61H 3/008; A61F 5/028; A61F 5/04; A61F 5/0193; A61F 5/026; A61F 2002/30062; A61F 2002/3055; A61F 2002/30617; A61F 2210/0004; A61F 2250/0007; A61F 2250/0018; A61F 2250/005; A61F 2250/0087; A61F 2250/0097; A61F 2/0045

USPC ......................... 602/19, 32–36; 128/874–875

See application file for complete search history.

(56) References Cited

U.S. PATENT DOCUMENTS

| | | | | |
|---|---|---|---|---|
| 3,167,068 | A * | 1/1965 | Carr | 602/32 |
| 3,234,568 | A | 2/1966 | Fischer | |
| 3,872,860 | A * | 3/1975 | Noblitt | 602/36 |
| 4,050,737 | A | 9/1977 | Jordan | |
| 4,099,524 | A * | 7/1978 | Cueman et al. | 602/19 |
| 4,739,526 | A | 4/1988 | Hollick | |
| 4,748,701 | A | 6/1988 | Marlowe | |
| 5,115,802 | A * | 5/1992 | Dyer | 602/33 |
| 5,502,851 | A | 4/1996 | Costello | |
| 5,647,138 | A | 7/1997 | Tang et al. | |
| 6,122,778 | A | 9/2000 | Cohen | |
| 6,196,229 | B1 | 3/2001 | Piazza | |
| 6,244,991 | B1 | 6/2001 | Bingham | |

(Continued)

*Primary Examiner* — Michael Brown

(74) *Attorney, Agent, or Firm* — Bruce M. Kanuch; Christopher John Rudy

(57) ABSTRACT

An improved patient garment for assisting a caregiver in lifting, and performing therapy evaluation and treatment techniques on a patient, without having to change slings for each task is provided. The garment comprises at least a pelvic belt having a width and length configured to fit around the waist of a human below the rib cage and above the hips and said length having an open front that contains at least one adjustable strap and buckle combination to secure the garment around a human torso, a top rim and a bottom rim; multiple fastening means attached to the garment along the top and bottom rims, and additional fastening means attached to the surface of the garment along its length and located between the top rim and the bottom rim of said garment. The invention can include other pieces of garments that are attachable to the pelvic belt and detachable there from depending on the function desired by the caregiver.

17 Claims, 25 Drawing Sheets

(56) References Cited

U.S. PATENT DOCUMENTS

| | | | |
|---|---|---|---|
| 6,276,006 | B1 | 8/2001 | Hoit |
| 6,752,776 | B2 | 6/2004 | West |
| 6,890,288 | B2 | 5/2005 | Bingham |
| 6,942,630 | B2 | 9/2005 | Behan |
| 7,945,975 | B2 | 5/2011 | Thomas |
| 7,979,919 | B2 | 7/2011 | Joran |
| 2005/0192159 | A1 * | 9/2005 | Jackson et al. .................. 482/23 |

* cited by examiner

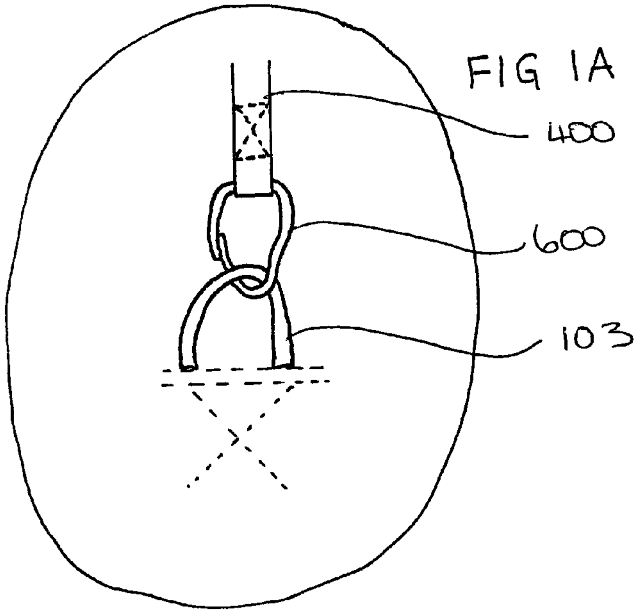
FIG 1A
FIG 1B
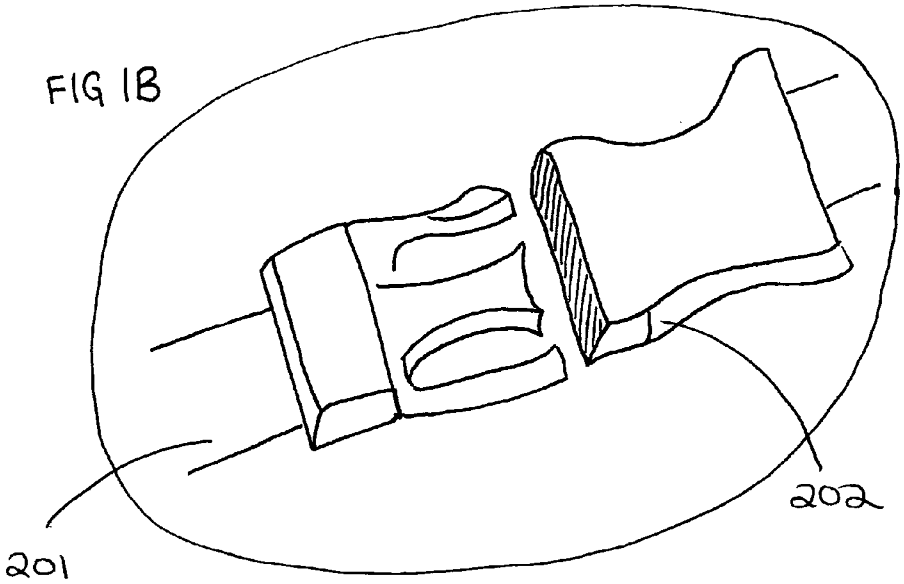

203
600
302

400
501
500
502
600
203
201
200
202
301
300

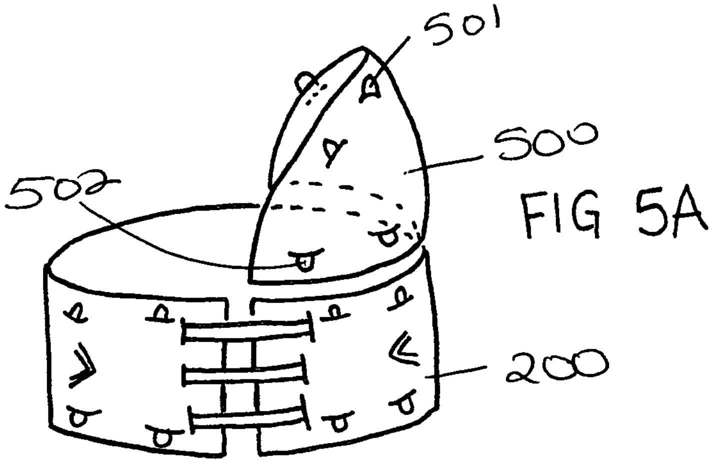
FIG 5A
FIG 5B
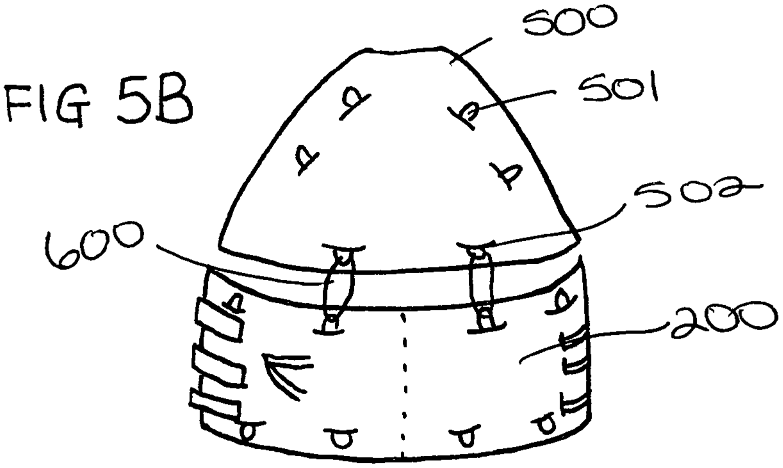

400
200
402
701
700

PROGRESSIVE MOBILITY ASSISTANCE GARMENT FOR REHABILITATION

RELATED APPLICATION

The present application relates to and claims priority to U.S. Provisional Application No. 61/632,886 entitled Progressive Mobility Assistance Garment for Rehabilitation filed Feb. 1, 2012, herein incorporated by reference in its entirety.

BACKGROUND OF THE INVENTION

1. Technical Field of the Invention

The present invention relates to a garment for assisting a person (e.g. a caretaker etc.) in the lifting, positioning or performance of therapeutic interventions of a second individual (e.g. a patient). The present invention relates to a garment (s) worn by the person requiring assistance that assists both the caregiver, and the person who needs assistance. Chance of injury to the caregiver is reduced and improved comfort and physical performance of the person requiring assistance is achieved.

2. Description of the Related Art

Current research shows continued high rates of work related musculoskeletal disorders among nurses and physical and occupational therapy practitioners resulting from handling and moving patients. Obesity indices show increasing numbers of patients who are overweight, and projected shortages of nurses and therapists makes it increasingly important to prevent such injuries. Over time a great variety of lifting and transfer devices have been developed that use a garment that must first be placed on the person requiring assistance. The garment/sling is then connected to a mechanical device that enables the caregiver to safely assist a patient in moving from one position or from one location to another.

Various examples of such garments and mechanical lifting devices that can be used in conjunction with such garments are disclosed for example in the following U.S. Pat. Nos. 3,234,568; 4,050,737; 4,739,526; 4,748,701; 4,981,307; 5,502,851; 5,647,378; 6,122,778; 6,196,229; 6,244,991; 6,276,006; 6,752,776; 6,942,630; 6,890,288; 7,945,975; 7,979,919.

There are four basic categories of mechanical lifts, each designed for a specific care task and each using a different designed sling to lower or raise the patient from one position to another.

The first category is the dependent lift. This lift comes in floor-based models, which are designed to be mobile and move from room to room, and ceiling lifts, which are built into the infrastructure of the ceiling in the facility, with tracking that the motor moves along, to allow lifting of patients from one position to another, to be boosted up in bed, or turned over in bed, or to be lifted from the bed to a chair and back etc. The slings or garments that can be used with these devices fall into four categories. One is a total lift sling that totally lifts the patient up and cradles them; the second is a walking, or ambulation sling. There are a few different types of walking or "ambulation" slings. One kind is a closed vest-type, with straps hooking from the shoulders to the lift. Another kind is a torso garment with straps from the waist to the overhead lift. The third category is turning or boosting slings, which are designed to roll the patient over or boost up or reposition in bed. The last category is limb slings which are basic straps designed to lift a patients' limb while caring for the patient. The caregiver must decide whether the patient is going to be lifted dependently, moved in bed or walk/ambulate, and choose the appropriate sling/garment.

Another type of lift is the powered sit-to-stand lift, which has a different specially designed "belt-type" of sling/garment, with straps that attach from the front of the torso on the sling to the device that raises the patient from sitting to standing. Each manufacturer of a lift has a different design of sling, but the basic concept is the same, with a belt around the waist/torso area, and straps attaching the sling to the lift. Some models of this kind of sling have an extra strap that slides below the buttocks to further assist with the lift.

The next progression towards patient independence is the pull-to-stand lift. This lift has a bar that the patient uses to pull himself up to a standing position. Some versions of this lift come with a "belt-type" sling/garment that hooks onto the lift for patient safety in case the patient leans back, but the patient still pulls himself to a standing position.

When patients are able to do most of the work themselves, the caregiver may choose to use a "gait belt" which is basically a belt around the patients' waist that has built in handles for the caregiver to hold onto in case the patient stumbles or falls. Gait belts come in a variety of designs, from a basic belt to a padded belt with fabric handles at various points.

Even with the wide variety in design and function of each of these lifting and transfer devices and slings/garments, each has its own inadequacies and limitations because each is usually designed for only one purpose. Hospitals and treatment facilities must purchase and keep on hand a great variety of assist garments and choose one when a certain function is performed, and another for a different function, and even then they do not satisfy the many needs that exist. Caregivers are also extremely busy and not having to switch from one garment to another would be a great time saver.

Additionally, for patient rehabilitation physical and occupational therapists have unique needs for handling patients. The goal of rehabilitation pushes the patient to do as much as they can for each mobility task. When a nurse gets a patient up their priority is to get them from bed to chair quickly and easily. When a therapist gets the same patient up, they are more focused on ensuring the patient does as much for themselves as possible with normal movement.

The other unique aspect of therapy is progression from one mobility task to another in succession during one treatment session. When a normal healthy person wants to get up out of bed there are several components or tasks they do to accomplish that. The therapist will break down this function into each task and assess how well the patient performs that task. For example, the therapist first assesses whether the patient can roll over onto their side in bed. If they can, the therapist notes how much assistance is required, then moves on to how the patient gets from lying on their side, to sitting on the edge of the bed, again, noting how the patient moves, and how much assistance is required. Once sitting, the therapist will assess sitting balance, and whether the patient can put their own socks, shoes and pants on, or how much and what kind of assistance they need to do this. They will also assess patients' ability to wash their face, eat, groom etc. From there, they will assess how the patient moves from sitting to standing. Again, technique, normal movement and level of assistance required are documented. Once standing, the therapist will assess patients' ability to walk, assessing how they move their legs, how much help they need, how far they can go, how hard they are breathing etc. All of these activities may be assessed in a single treatment session. Once the therapist has determined where the patient is having difficulties, those activities become the treatment plan to help restore normal movement to those activities and progress the patients' independence. This is one example where the invention provides great assistance.

As the patient changes position, the hand placement for assistance provided by the therapist and the angle of force required to assist the patient changes. In assisting a patient in rolling over in bed the therapist will pull forward on the patients' pelvis and hip area, pulling horizontally towards themselves. Once the patient is lying on their side, to assist the patient to a sitting position, the therapist will grasp under the patients' shoulder and rib cage, and lift upwards and towards the patients' feet, at an angle of approximately 45 degrees. The angle changes as the patient approaches upright, and is then more horizontal as they approach sitting position. This helps bring the patients' torso up to a sitting position. Once sitting, the therapist often needs to prevent the patient from falling. The patient can fall in any direction, so the direction of forces changes for the therapist. In this position, the ideal angle of assistance is directly vertical to hold the patient in a sitting position, although in some situations, for example if the patient has had a stroke, they can "push" to one side or they may have no muscle tone on one side and fall to that side, in which case more support may be needed on one side or the other.

For helping the patient move from sitting to standing normal movement is the goal, so the angle of assistance provided by the therapist changes again. This time the assistance needs to come from the patients' pelvis, upwards and forwards, to assist the patient to a standing position. Once standing, the vertical support would be the preferred angle of support, as again, the patient can fall or stumble in any direction.

Currently there is no one assist garment that can be used to perform several of these functions. Some garments will accomplish two tasks, e.g. a dependent sling can be used to get a patient out of bed and turn a patient over; but there is no garment to assist with the side-lying to sitting portion of the task, and the caregiver/therapist has to switch from one sling to another for each task they wish to assess or work on. Therapists continue to have to manually move or reposition patients resulting in persistent high injury rates to therapist. Therapists also resist using the safety lifts and devices because current slings/garments prohibit "Normal" movement. This is an important component for proper patient rehabilitation. When the therapist has identified the specific area that the patient is having problems, treatment will be aimed at practicing this component of the task over and over so that the patient gets stronger or re-learns how to complete that component of the task, thereby enabling them to become more independent, and require less assistance for performance of the task. The nature of this means therapists are putting themselves in harm's way over and over again, as they are providing the manual assistance to the patient over and over again. Frequently treatment sessions are terminated because of the therapists' fatigue level, rather than the patients' fatigue level. Because of the limitation of available slings/garments, there is often no way around this for the therapist. The result is both risk of injury to the therapist, and risk of not maximizing progress for the patient.

The prior art waist or "gait" belts have limited assistive value. A gait belt is a padded or non-padded belt that fits around the patient's lower rib or waist area and can come with multiple handles that are used to support the patient should they start to fall. Some of the commonly known drawbacks of gait belts include: 1) they can be uncomfortable for the patient, 2) they have a tendency to slide up during transfer, and 3) gait belts will not prevent a patient from falling. They may help stabilize the patient if they just lose their balance momentarily, but for prevention of caregiver injury, their effective use is limited to patients who only need minimal assistance, or "a guiding hand".

Most of the slings/garments that are available for the sit-to-stand devices do not promote normal motion for a patient coming from sitting to standing. They are designed to "lift" a patient up from sitting so that the patient can be transferred to a chair or back to bed. Most models require the patient to "just lean back" and let the machine bring him up to standing. Some models do encourage more normal movement, but the garment/sling perform only this function. Moreover the slings have a tendency to ride up under the patients' arms. Once the patient is up, the angle of pull of this sling/garment is not ideal for ambulation, and the patient can only ambulate in the device that the sling/garment is designed for. If the therapist wants to progress the patient to a different activity, they must first take this sling off and switch to a different garment.

One other available sling/garment on the market in the field of therapy is the "Lite Gait" sling. This sling is designed to help a patient ambulate on a treadmill. The sling/garment supports some of the patients' body weight thus enabling them to walk more easily. The sling/garment is suspended from an overhead bar on the "Lite Gait" frame. The application of this garment is limited to only this function. The other tasks that have been mentioned earlier are not helped by this sling/garment.

Another similar garment is taught in U.S. Pat. No. 6,302,828. This standard unweighting harness is used for ambulation, however, it will not function for bed mobility tasks and can only be used with a vertical sit-stand assist lift, which is not normal movement, and is not helpful in retraining a patient to perform this task normally. Further products such as Lokomat™ driven gait orthotic that automates locomotion therapy on a treadmill and improves the efficiency of treadmill are known. It is a robotic assistance training tool which uses a harnesses to take weight off of the body. However, once again, these harnesses are designed only for ambulation and not for the other tasks described, One key feature to note in most of the slings/garments that are available is that the straps that interact with the mechanical devices are fixed onto the garment, in a fixed location with a fixed or limited availability to change the angle of pull. This is a key difference of the described invention that sets it apart from other garments currently available. The invention includes multiple points for attaching and detaching straps that can be moved to apply assistive force in any direction, from any point on the patients' torso and pelvis. For effective rehabilitation and therapy, multiple different pull angles and multiple levels of assistance within these angles are often required by the therapist in one treatment session with the patient. Variability, not only of the angle of pull, but of the level of assistance provided by the lift and strap/garment combination is essential, for a multitude of positions and mobility tasks. Another improvement offered by the invention and not the prior art is the ability to have an elastic component to the straps for varied levels of assistance or support provided to the patient. This enables a therapist to "Make a patient work on a specific task". In rehabilitation of patients, especially if the patient has suffered damage to the brain where they must re-learn a movement, they must practice a task over and over. When the goal of rehabilitation is to improve the patients' strength, the therapist must progress the patient to increasingly difficult tasks, as the patient accomplishes one level.

An example of this is a patient who needs strengthening for their shoulder. In any therapy clinic, you will see stretchy, elastic bands of varying colors. The therapist will first choose a light resistance to have the patient work against, then as the patient improves; the therapist will make it harder by giving the patient stronger and stronger resistance for them to work against. This is a universally accepted method of patient functional progression for limbs when the patient can do the work themselves.

By comparison, when the weakness is located in the patients' trunk, for example when they are not even strong enough to hold their weight up against gravity, far less added resistance is needed, the same principle is used in reverse, to help them progress. When a patient has little to no trunk strength, the therapist(s) provide "maximal" assistance. This is referred to as "the patient is totally dependent". The assistance is provided by the physical strength of the therapist. Once the patient progresses a little, the therapist(s) then provides "Moderate" assistance. This means that the therapist does a little less work and the patient does more. The next level is labeled "minimal" assistance. Max assist means that the patient does less than 25% of the work, and the therapist does the rest of the work. Moderate has the patient expending 25-49% of the work and the therapist doing the rest etc. The current art provides no way for a therapist to use equipment and/slings to progress a patient in this manner. The "progression" comes purely from the variable amount of assistance provided by the therapist. In many cases, this results in therapists lifting upwards of two tons per day.

The invention provides an assist garment that permits the use of progressive resistance straps to provide the described progression, thus taking advantage of the theory behind using progressive resistive bands for shoulders. For maximal assistance to the patient, a strap with strong elastic would be used, i.e. little "give" to it. As the patient gets stronger, a strap that has more "give" and more elasticity would be used. Once the patient can tolerate holding themselves up against gravity, the straps could resist the movements by changing the points of attachment and points of pull. For assistance, they would be placed in synergy, or along the intended path of the patient movement; for resistance, they would be opposing the desired movement.

The economic climate in health care means fewer staff is expected to see more patients. Stiff competition for clients has led to the need for efficiency and competitive patient outcomes at the same time. Facilities are benchmarked against each other based on how much better their patients get, in what period of time. There are also increasing financial incentives for facilities to out-perform their competitors. These factors mean that the pressure on therapists and caregivers to get patients better quickly is great. Time is a short commodity in most healthcare facilities. Time and ease of use of safety devices and slings is critical. Current garments and slings are not conducive to progressive patient mobility with minimal extra time for the caregiver. The result is those caregivers do not use safety equipment, instead, putting themselves, and sometimes their patients at risk for injury. The invention helps to achieve these beneficial results.

Certain patents and publications have disclosed concepts associated with assisting handicapped or incapacitated patients, but none meet the needs filled by the present invention. U.S. Pat. No. 6,122,778 issued Sep. 26, 2000 to Cohen describes a loose-fitting vest or garment which enables caregivers to assist a patient in moving from one position to another. Similarly, U.S. Pat. No. 5,647,378 to Farnum discloses a lifting support belt constructed of an elastic, flexible rubber-like material and includes a plurality of flexible handles, which are fixed to the belt in a spaced apart relation. The Farnum design requires the length of the belt be customized to fit different sized individuals. While useful in some situations, the handholds of the Farnum design do not provide adequate leverage to a caregiver in all situations. The Farnum design includes no means for grasping a patient's chest or shoulder area. U.S. Pat. No. 6,244,991 shows a one piece garment having multiple fasteners, 63 and 62 but this garment would be almost impossible to put on an invalid or incapacitated patient because its one piece construction and having both leg and arm holes.

SUMMARY OF THE INVENTION

The invention comprises a patient assistance garment configured to be worn on the torso of a patient that provides assistance to a caregiver comprising; a pelvic belt having a width and length configured to fit around the waist of a human, the width extending from the lower ribs to the hips and said length having an open front that contains at least one adjustable strap and buckle combination to secure the garment around a human torso, a top rim and a bottom rim with multiple fastening means attached to the garment close to the top and bottom rims, and additional fastening means attached to the surface of the garment along its length and located closer to the center width than the fastening means located close to the top rim and the bottom rim of said garment. This garment comprises the core of the invention. Additionally and optionally other pieces such as, thigh/crotch support straps; rib/chest pad; open front vest: torso/limb straps; and connectors, that can be connected to and released from the core pelvic belt are provided.

The spirit and scope of this invention is the ability to quickly modify the functionality of the garment to adapt to different uses. For variations in patient care, modifications may include, more or less support strapping, different placement of tightening devices and mechanisms, alteration of the straps for maximum versatility and comfort, alterations in materials used to improve infection control and ease of application to the patient etc. The elastic concept, that allows the therapist to assist or resist certain movements can also be adapted to improve limb function, such as changing thigh straps to attach the thigh supports to elastic assistance on the front to assist lifting the hip forward, or on the back to resist forward movement of the hip during walking, adding arm straps with similar concepts to assist or resist upper extremity function in combination with the previously described functions of the invention. This feature has not been seen in prior art garments. The invention provides the ability to add and remove pieces, change angles, change tension strap attachment points and the tension provided by the straps, and change the function of the sling depending on how you build or assemble it.

BRIEF DESCRIPTION OF THE DRAWINGS

A more complete understanding of the method and apparatus of the present invention may be had by reference to the following detailed description when taken with the accompanying drawings, wherein:

FIG. 1A is a blow up of circled portion of FIG. 1 showing the connection between a support strap 400 and an attachment loop fixed on the shoulder of the vest, 100.

FIG. 1B is a blow up of the circled portion of FIG. 1 showing the strap and buckle of the vest 100.

FIG. 5 also shows optional adjustable straps located on the back of the pelvic belt for adjusting the length of the belt.

FIGS. 5A and 5B illustrate just the rib/chest pad and the pelvic belt connected at different positions, side and back.

Figure 1:
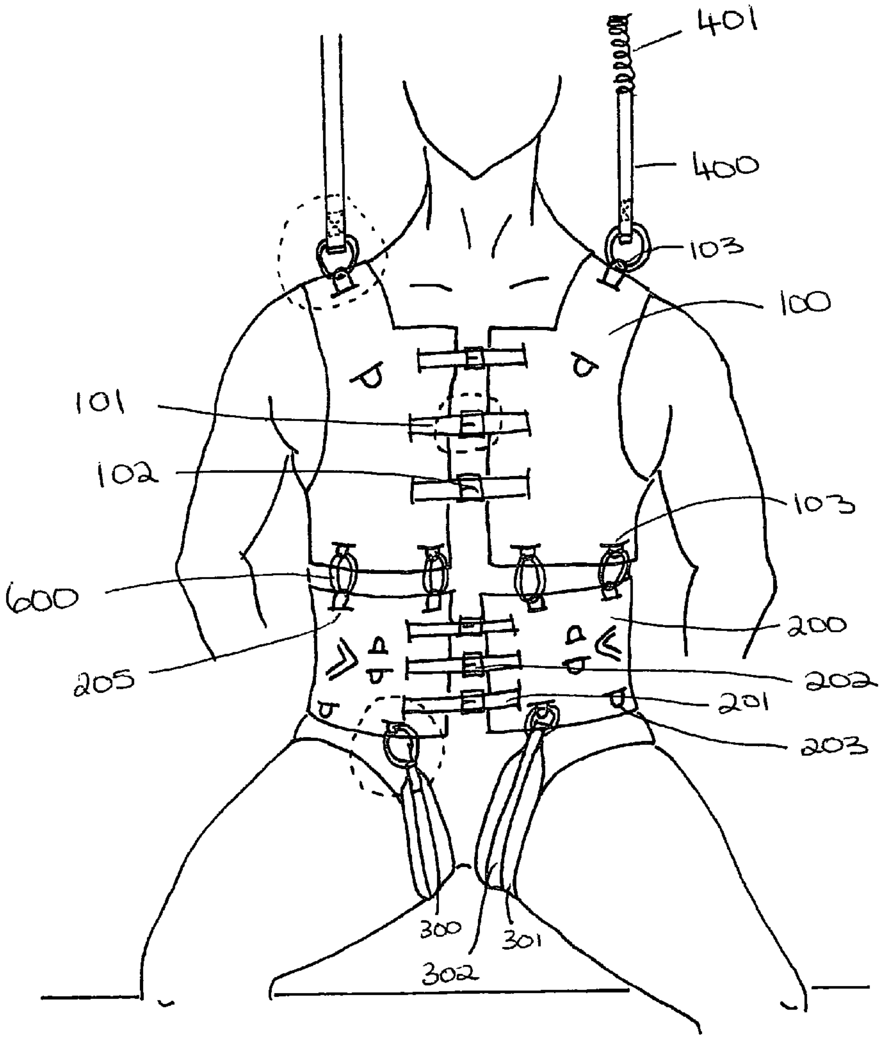
FIG. 1 is a front perspective view of the patient assistance garment of the present invention worn by a person. In this view, the patient is wearing a vest 100, a pelvic belt, 200; and two crotch supports, 300. The garment is attached to a connector strap on the left and right shoulder comprising a combination of one rigid connector strap, 400 and one elastic connector strap, 401. The straps are connected to a mechanical lift device not shown. The vest and crotch supports are attached to the pelvic belt in a manner that they can be easily detached if desired.

Where used in the various figures of the drawing, the same numerals designate the same or similar parts. In some Figures not all the parts are numbered and when not the part is to be regarded as the same part as numbered in other drawings. When the terms "top," "bottom," "first," "second," "upper," "lower," "height," "width," "length," "end," "side," "horizontal," "vertical," and similar terms are used herein, it should be understood that these terms have reference only to the structure shown in the drawing and are utilized only to facilitate describing the invention.

All figures are drawn for ease of explanation of the basic teachings of the present invention only; the extensions of the figures regarding number, position, relationship, and dimensions of the parts to form the preferred embodiment will be explained or will be within the skill of the art after the following teachings of the present invention have been read and understood. Further, the exact dimensions and dimensional proportions to conform to specific force, weight, strength, and similar requirements will likewise be within the skill of the art after the following teachings of the present invention have been read and understood.

It is intended that with the multitude of drawings and teachings, that the unique characteristics and improvements provided by the invention will be fully demonstrated. The invention provides for a wide variety of patient treatments not provided by assist garments/slings disclosed in the art.

Patients can be supported in any position, as much or as little as needed, with assistance or resistance as desired by the therapist for the desired mobility task.

DETAILED DESCRIPTION

In the FIG.s and the following detailed teachings the numbers have the following descriptions:

100: An open front vest that can be attached and released from the pelvic belt 200. It can be made of a flexible, durable material that and preferably is made from a material that can be wiped with anti-microbial agent, be laundered, or include a liner for protection against contamination for infection control. This piece fits like a life jacket which, as shown in this embodiment, includes three adjustable length web strap/buckle combinations to close the front of the vest. The webbing is preferably wipeable with an anti-microbial agent, and the buckles can be plastic parachute buckles or ghost buckles that can be easily released and wiped down for infection control. The vest is provided with a plurality of attachment means affixed to the material of the vest, such as D rings or webbing loops, 203, which can be used to attach to corresponding loops on other garment pieces, or will provide means for attaching assist straps 400 that can be used by a care giver or which are attached to various lift devices. The placement of the loops in the shown embodiment is one on each shoulder, one on each chest area midway between the neck and waist edges of the vest and midway between the center and the axilla (armpit). Exact location of the means of attachment e.g. loops may be varied. The attachment means are also attached along the lower edge of the vest so that it can be attached to the pelvic belt. The scope of the invention does not limit location of attachments, but rather, promotes the flexibility to locate them as needed, as further uses may become apparent. The versatility and plurality of attachment means choices is an important feature of the invention. There are also preferably at least two means for attaching located on the back of the vest. The means for attaching other pieces can be sewn into the fabric of the vest. In the shown embodiment there are also included eight attachment means located along the lower edge (hem) of the vest which can be used to attach the vest to the eight attachment means shown on the pelvic belt 200.

101: Length adjustable strap to tighten or loosen the vest straps to fit different patient sizes.

102: Buckle attached to strap 101 for example a two-way adjustable buckle.

103: Webbing loops or D rings attached at intervals along either side of the vest or shoulder straps 800 to provide attachment points (means) for connector straps. These loops can be comprised of a strong webbing or similar material or D rings, which can be stitched to the vest or straps in a figure "8" pattern for extra strength, with the loop section free to provide easy attachment via connector straps or clips, such as the carabineer, 600, or the connector straps, 400.

200: Pelvic belt that is the core component of the invention that will in most situations be used in all applications. This is comprised of a durable, flexible material that will either be made of a material that can be cleaned such as wiping with an anti-microbial agent, or has a liner that achieves infection control, or a material that can be safely laundered. This is a flexible circular belt that conforms to the patients' pelvis and lower waist. In the embodiment in the drawings there are three adjustable webbing straps attached in the front with buckles, such as parachute buckles or ghost eye buckles for opening and closing Additional adjustable webbing straps may also be attached on the exterior of the garment in the back, (205) for additional tightening of the belt if needed (such as by gathering the material.) The garment is preferably flexible enough that additional tightening in the back will be comfortable for the patient. The pelvic belt is illustrated with 8 webbing loops, sewn onto the fabric and reinforced for strength, along the upper border of the garment, and 8 webbing loops, similarly sewn into the lower border of the garment. These loops will provide means for attaching additional garment components, by virtue of for example Carabineer-type clips attached to loops or other forms of attachment (e.g. D rings sewn to the belt), located on other pieces of garment such as the padded straps 800, or thigh straps, vest, assist straps and the like. There are also shown in these embodiment four loops sewn into the pelvic belt, at intervals to provide one midway between the center and the lateral angle of the patient on each side, and similarly, one on each side in the back, midway between the center and the lateral angle. Again, the exact location may be changed to provide different or improved function of the garment. The spirit and scope of this invention is the plurality and versatility, and changing location to meet needs is within the scope of the invention, rather than exact location of attachment means e.g. webbing loops.

201: Webbing adjustable strap attached to pelvic belt for opening, closing and adjusting tightness of the belt.

202: Buckle

203: Multiple webbing loops or other attaching means such as D rings fixed to the pelvic belt along and close to the lower border of the belt.

204: Multiple webbing loops or other attaching means such as D rings along and close to the upper border of the pelvic belt. (8)

205: strap/buckle combination located on the back side of pelvic belt for additional adjustment of length of the belt.

206: An extension piece (FIG. 2) that can be added in front of the pelvic belt for use with larger patients. It has three corresponding straps/buckle combinations on each side, to communicate with the portions of the straps on the main pelvic belt garment. Parachute buckles will communicate with male/female connections to connect the two pieces.

300: Thigh/Crotch support strap. In one embodiment as shown in FIG. 1 the support comprises a padded webbing strap encased in a casing, with thickness enough to be comfortable for the patient. This is preferably covered with a wipeable material and/or a liner that achieves infection control, or be of material that can be safely laundered. Two of these straps are attached to the pelvic belt to aid in supporting a patient. In another embodiment shown in FIG. 6 as 300*a* and as a dashed line in FIG. 5 the support is formed in an X-shaped strap having two tails at each end and a broader middle portion that supports the patient's weight when standing and walking. The straps have carabineer-type clips on the ends to interface and attach with the loop attachments attached along the lower border of the pelvic belt. The strap has an adjustable length webbing strap. The support straps can also have attachment loops, 302, fixed to it that can be used to connect with other sections of the garment.

301: The parachute buckle/webbing combination for adjustability

302: Webbing loops fixed at intervals along each border of the short/thigh/crotch strap.

303: Means for attaching and releasing the crotch support to the pelvic belt.

400: Depicts assist straps (connection straps) that attach to various pieces of the garment and interface (connect with) with mechanical assist devices (lifts) that provide mechanical assistance. The assist straps can also be used by the caregiver to assist the patient when appropriate.

401: Spring/tension connection means such as attached springs of different tensions, or elastic straps of various tensions. These will also have attachments at each end such as carabineers or the universal connector 900, that attach to the required mechanical or non-mechanical device.

402: Short attachment strap for shorter attachments such as to attaching the thigh/crotch straps, 300 or 700 to the pelvic belt, 200.

500: Rib/chest pad. This is shown with a symmetrical front and back appearance, but could also be extended in the back portion, to come up under the patients' shoulder blade for increased support in key mobility tasks. The pad is generally in the shape of a semi circle. Pads are sized to be attached to the pelvic belt via the attachment means fixed to both the belt and the pad, e.g. webbing loops.

501: Webbing loops or other attaching means, e.g. D rings attached along the upper border of the rib/chest pad 500 for attachment of assist straps 400.

502: Webbing loops or other attaching means, e.g. D rings attached along the lower border of the rib/chest pad 500 for connection with the pelvic belt.

600: Carabineer clip as an example of a means to connect various garment pieces together via the attachment means fixed to the various garment pieces.

700: Thigh supports that can be used as an alternative to the crotch supports. They can be connected to the pelvic belt in the same manner as the crotch support or an extended strap 402 can be used. The thigh support (garter) is adjustable in length. It attaches to the pelvic belt and one is usually used on each leg of a patient.

701: Webbing loop to connect via connection straps to loop-style lifts or can be used by caregivers to treat the patient with use of bungee cords or the like.

702: Thigh straps to attach the thigh supports to the pelvic belt.

800: Long padded straps (2 per kit), which can used for example instead the vest 100. They can also be used for other functions such as to support the arms or legs of a patient. They can be made of a flexible, durable material that can preferably be wipeable with anti-microbial agent, be laundered, or include a liner for protection against contamination for infection control. These straps can be used parallel to each other, or crisscross across the front or the back or the side of the body, to add support as needed through the torso area. In one embodiment the straps are made from a casing through which a webbing strap is fed, and the webbing will have two way adjustable buckles that will allow easy adjustment for a snug fit. The casing can be split in the mid-section, for ease of access to the adjustable portion of the strap. The webbing is preferably wipeable with an anti-microbial agent, and the buckles can be plastic parachute buckles or ghost buckles for example, that can be easily released and wiped down for infection control. The straps will have a plurality of attachment means affixed to the material, such as webbing loops, 103 as used on the vest for example, which can be used to attach with corresponding loops on the other garment pieces, or will provide attachments for the assist straps 400 to be also attached to various lift devices. The placement of the loops in one embodiment is shown in the drawings at intervals along the length of the straps. Exact location of the loops may change as use of the mobility garment guides. The scope of the invention does not limit location of attachments, but rather, promotes the flexibility to locate them as needed, as further uses may become apparent. The versatility and plurality of attachment choices is the important feature. Although named the padded straps, it is also within the scope of the invention and intended use of the product, that this could also be used as a limb sling, supporting, for example a patient's thigh, and attached at either end, by the carabineer, and universal connector, to the mechanical device of choice

900: Universal connector comprised of an "o" ring 900*a* that has a webbing loop sewn to it, 900*b*, as well as a clip attachment sewn onto it 900*c*. This will serve to connect the straps (400, 401) to the various lift devices. Some models of the lifts use the clip attachment, some use the loop attachment.

The invention includes at least a basic pelvic component, 200, having attached to the surface thereof multiple attachment means for attaching both additional garment pieces and also attachment of assist straps, and ability to add or remove extra support as needed for the patient task that is being performed. The pelvic belt wraps around the patient's trunk and comfortably transfers load to the lower abdomen, over the hip, and through the groin.

Additional garment support pieces optionally include, padded straps 800 that can be used to support various parts of the upper or lower body, a rib/chest pad piece 500, each with multiple points of attachment means, such as carabineer clips, for attaching the various pieces together and other means for attaching other useful members such as assist straps 400; crotch/thigh members 300 or thigh supports 700, for example if the patient has a catheter, variable assist straps such as variable strength bungee cords 400, that will allow rigid to minimal assistance to a patient, a vest piece, 100, and universal connector member 900 that can interface with various styles of mechanical assistance devices. One or more of these pieces can be supplied as a kit to caregivers.

The multiple attachment means allow for many combinations of assistive angles. The horizontal forces required for assisting patients to roll over will direct the therapist to use one set of assist strap attachments; then, if the therapist wants to work from side lying to sitting, they can then simply attach the rib/chest pad, 500, to the patient, for example, and move the straps from one point of attachment to another, or use two long padded/torso straps 800, crossed under the rib cage, to change the angle of pull to pull upwards and towards the patients' feet to assist with that task. If the therapist wants to work on that task with the patient, they can attach an elastic or spring loaded strap, 401, that can adjust how much assistance the patient is given for the task. The patient is then encouraged to engage maximal effort and let the machine/sling/strap combination do the additional work, not the therapist. Once sitting, the straps can be attached to an overhead lift to assist with sitting balance, by moving them to the vertically oriented attachments. If the therapist then moves to sit-stand activity, they can choose to reattach the straps on the sling/garment that will pull the patient up and forward, if the therapist uses the powered sit-stand lift, or, if the therapist wants to have the patient use their own walker, the straps can be attached to an overhead lift either floor based or ceiling based and the patient can be allowed a greater degree of freedom to do more for themselves, with the safety of knowing they will not fall. The therapist can also choose at that time to attach the thigh straps under the crotch, which will prevent the pelvic belt from riding up, and will take some of the patients' weight if needed. If the patient has a catheter, or for patient comfort, the thigh strap attachments 700 can be used around the thighs. The thigh straps are adjustable length wise and vary in width from a few inches to twelve inches or more. One of the important improvements offered by the invention is it's the flexibility and universal utility to assist caregivers in performing multiple patient care functions by changing the strap placement, adding or removing the garment pieces, and choosing between rigid or elastic straps for more or less assistance. The key difference is the ease and speed with which the angles and functions can be changed, all with the same garment/sling, assisting the therapists with the challenge of progressive patient mobility, maximizing patient function, while protecting their own backs, necks and shoulders from injury by allowing the mechanical devices to do the “bull-work” and allowing the caretaker to focus on the treatment of the patient.

Another key advantage of this invention is the therapists' hands can be freed up to facilitate the patients' muscles to move normally. When the therapists are using their efforts just to hold the patients up, it is difficult for them to maximally cue the patients using their hand placements, to help the patient know what normal versus abnormal movement feels like. For patients who have had a stroke, or brain injury, this is vital. The current invention will allow therapists to choose how much support to give the patient, have that support provided by the lift/device and sling/garment, and leave their hands free to facilitate as needed. They can also appropriately push the patient to the patients' tolerance, not their own.

A continuing need exists for an improved transfer and repositioning garment that assists caregivers in lifting and moving patients in a wide variety of scenarios. Further, a need exists for an improved lifting assistance garment easier to put on and take off. A need also exists for an improved lifting assistance garment that is more easily adjustable to a wide variety of patients and a wide variety of different functions such as lifting patients to a sitting position from the prone position, rolling patients over, assisting patients from a bed to a wheel chair, permitting patients to engage in physical therapy.

The present invention overcomes many of the disadvantages of prior art lifting assistance garments. The improved patient assistance garment includes several separate garment pieces each containing a plurality of strategically positioned means for attaching other pieces of garment, such as hand holds, bungee lines and or straps which can be interchanged depending on the function desired. The invention can also include a pair of torso/long padded straps, at least a rib/chest pad and at least a lumbar/waist garment (pelvic belt 200) that have means for fastening the different pieces together and also having a plurality of means for attaching other pieces such as crotch or thigh supports, lines, bungee cords and the like. The assistance garment can be provided in the form of a kit containing various parts that can be assembled together by a care giver as needed.

Referring to the Figures and in particular FIG. 1 an embodiment of the patient assistance multiple piece garment of the present invention is shown. The patient assistance garment comprises a vest 100, a pelvic belt 200 and a pair of thigh/crotch support straps 300, shown as worn by a patient. The garment assists caregivers in lifting and moving the patient in a wide variety of scenarios. The garment is designed to be easily donned and removed from a patient.

The pelvic belt 200 and other garment pieces are constructed of a flexible, durable material. In one embodiment the material comprises a dense cotton denim type of material, or a vinyl over foam-type of material that can be wiped down. Other materials include, for example, bobbinet fabric, that is lightweight yet strong and durable. With materials that cannot easily be wiped down to clean, a liner could be used to protect against contamination for infection control purposes. Other materials can be used to construct the garment that is strong, yet flexible and lightweight, and comfortable for the patient.

The assist straps 400 are generally constructed of a reinforced webbing material that is flexible but stretch resistant. In a preferred embodiment the support straps comprise ballistic nylon webbing. The adjustable length is achieved by means of an adjustable length parachute buckle.

When graduated resistance is required, the assist straps can be made of elastic material 401, such as bungee cord of variable elasticity. The cord can for example be embedded in a webbing sleeve, so as to spread the force of the strap over a wider area for patient comfort. This will also prevent pinching of the patient, similar to the concept with a baby jumper that attaches in a doorway, allowing the baby to jump up and down.

Figure 17:
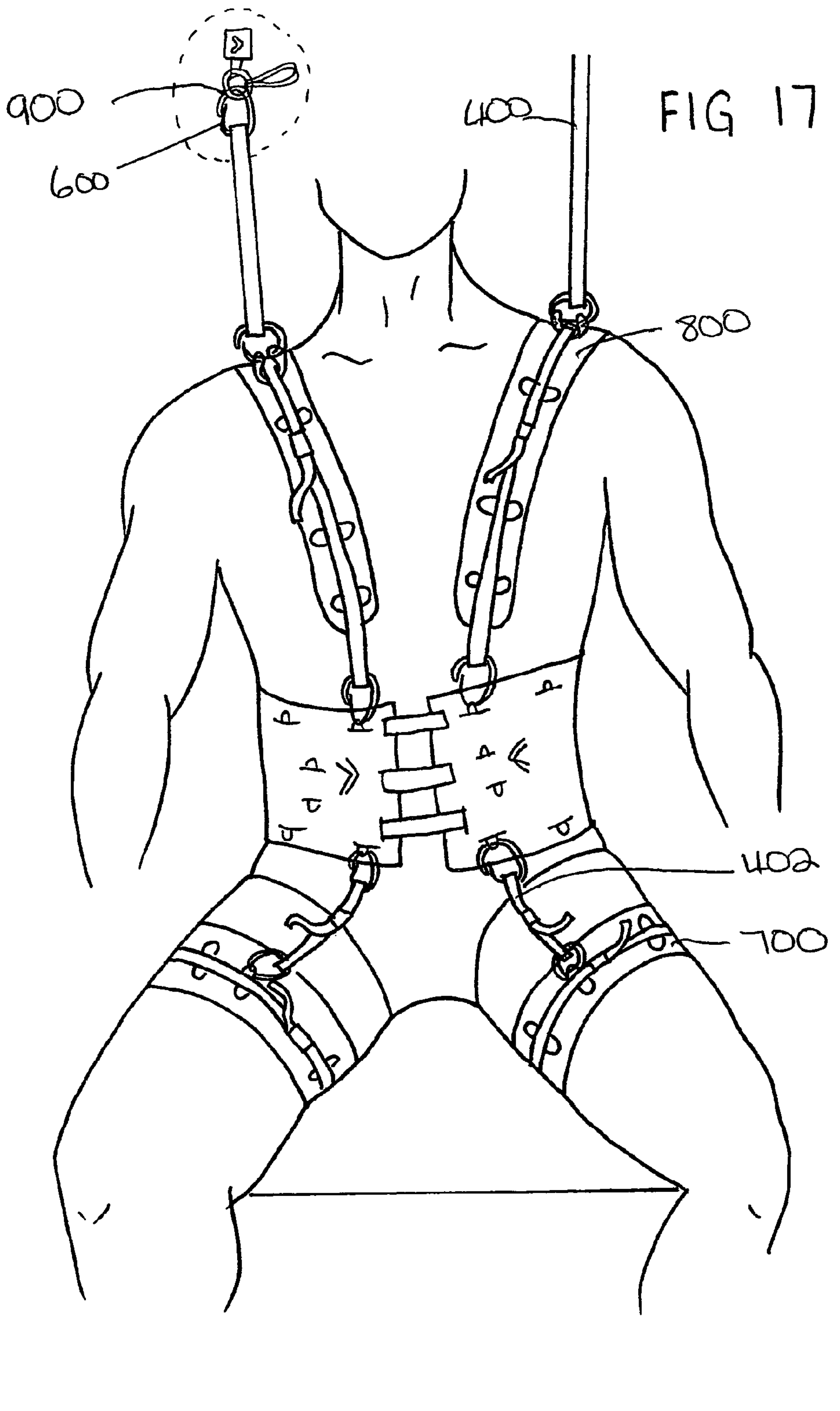
FIG. 17 illustrates the use of long padded straps, 800, in place of a vest 100 using the same pelvic belt.
Figure 17A:
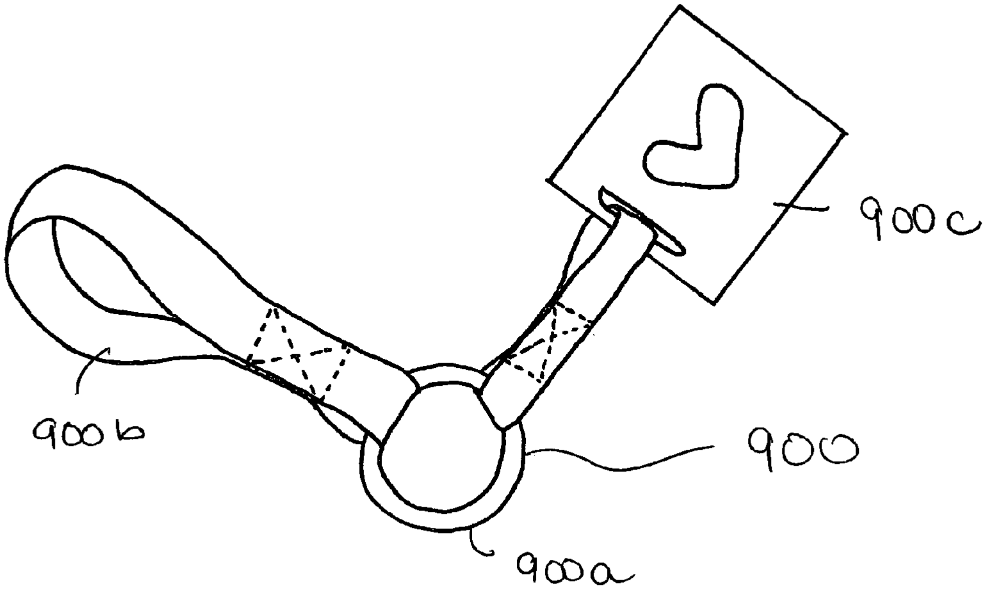
FIG. 17A is an enlarged potion of the circled part of FIG. 17 showing a universal connector, 900, that can be used to attach the assist strap to different lift devices.

In FIG. 1, the patient is sitting, and full support is employed, with the pelvic belt, 200, the vest, 100 and the thigh/crotch supports, 300. The assist straps, 400, are attached to the vest via the attachment means, e.g. webbing loops, and will connect at the opposite end to, for example, an overhead boom from a floor-based lift, or a ceiling lift, by means of the universal connector, 900, with hanger bar for attachment of slings. The therapist can work on the patients' sitting balance or reaching activities without fear of the patient falling over. Without the support, the therapist must take the full weight of the patient. This arrangement of the various pieces of the invention allows maximum access to the patient for the therapist to skillfully apply therapeutic intervention, without having to hold the patient up manually. From this position, the overhead straps can be made more flexible by adding springs/elastic component, 401, and the patient could then have “supported give” to reach forward and practice putting on their own shoes and socks without fear of falling over. FIG. 17 illustrates another embodiment where long padded straps 800, having multiple attachment means, are used instead of a vest.

Figure 1C:
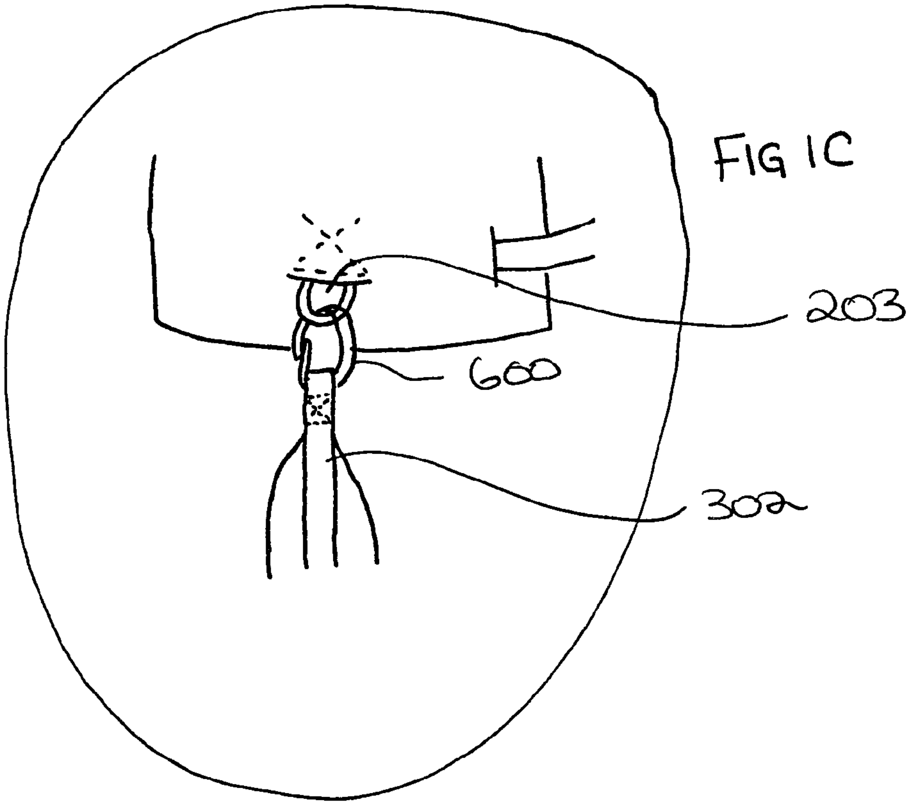
FIG. 1C is a blow up of the circled portion of FIG. 1 showing connection between the pelvic belt and the crotch support.

FIGS. 1A, 1B and 1C illustrate blown up circled portions shown in FIG. 1. FIG. 1A shows the attachment of the assist strap 400, to vest through the use of carbineer 600 and the webbing loops located on the shoulders of the vest 100. FIG. 1B is an example of a buckle/strap combination to close the front of the open vest. FIG. 1C shows the attachment of the pelvic belt to the thigh/crotch supports, 300 via attachment means fixed to the lower portion of the belt.

Figure 2:
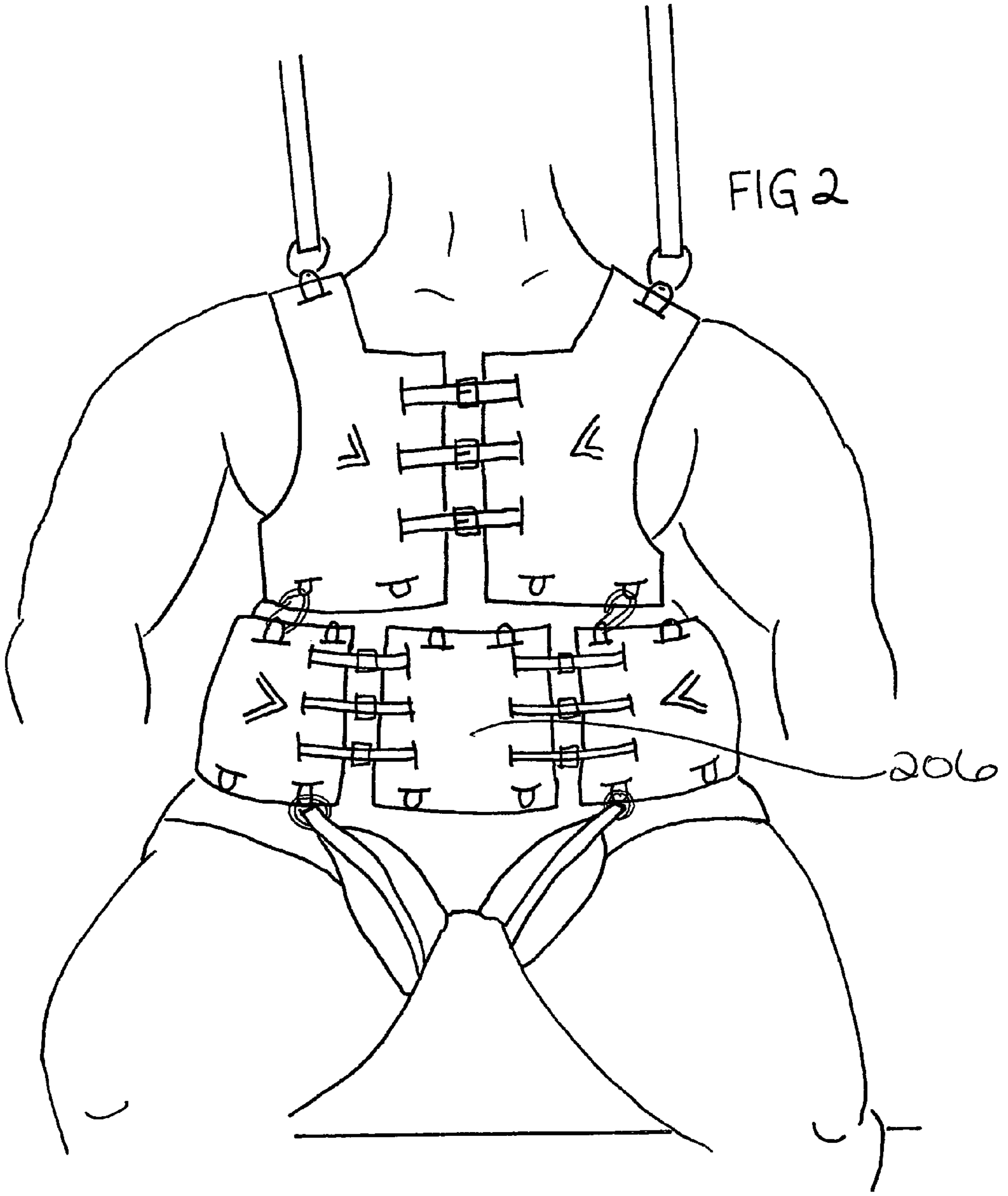
FIG. 2 is similar to FIG. 1 and shows in addition an optional girth adjustment garment 206.

FIG. 2 is the same as FIG. 1 except an optional extension piece, 206 is used to increase the size of the pelvic belt for a larger girth. A similar piece could be used expand the chest size of the vest.

Figure 3:
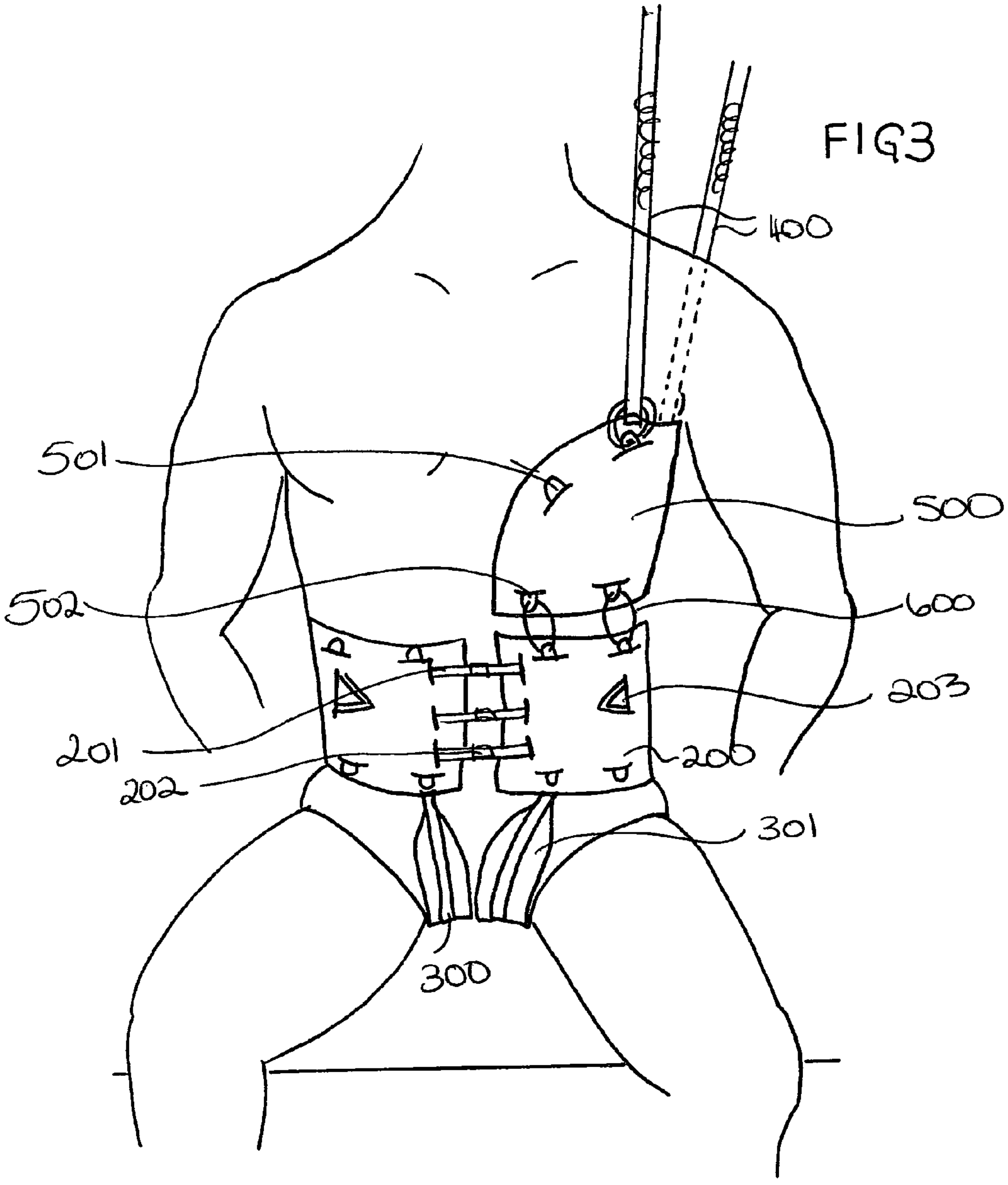
FIG. 3 shows the same pelvic belt core piece 200, with detail showing loop attachment, 201, parachute buckle, 202, horizontal loop attachment, 203, the vest 100 removed and replaced with a rib/chest pad 500 having multiple attachment means such as webbing loops. Loops are located along the top rim, 501, and along the bottom, 502. The rib pad is connected with a carabineer connector, 600. Thigh straps are shown, 300.

FIG. 3 shows a similar position as FIG. 1 except that a rib/chest pad 500 replaces the vest. This arrangement can be used when a patient might need more support on the left or side than centrally.

Figure 4:
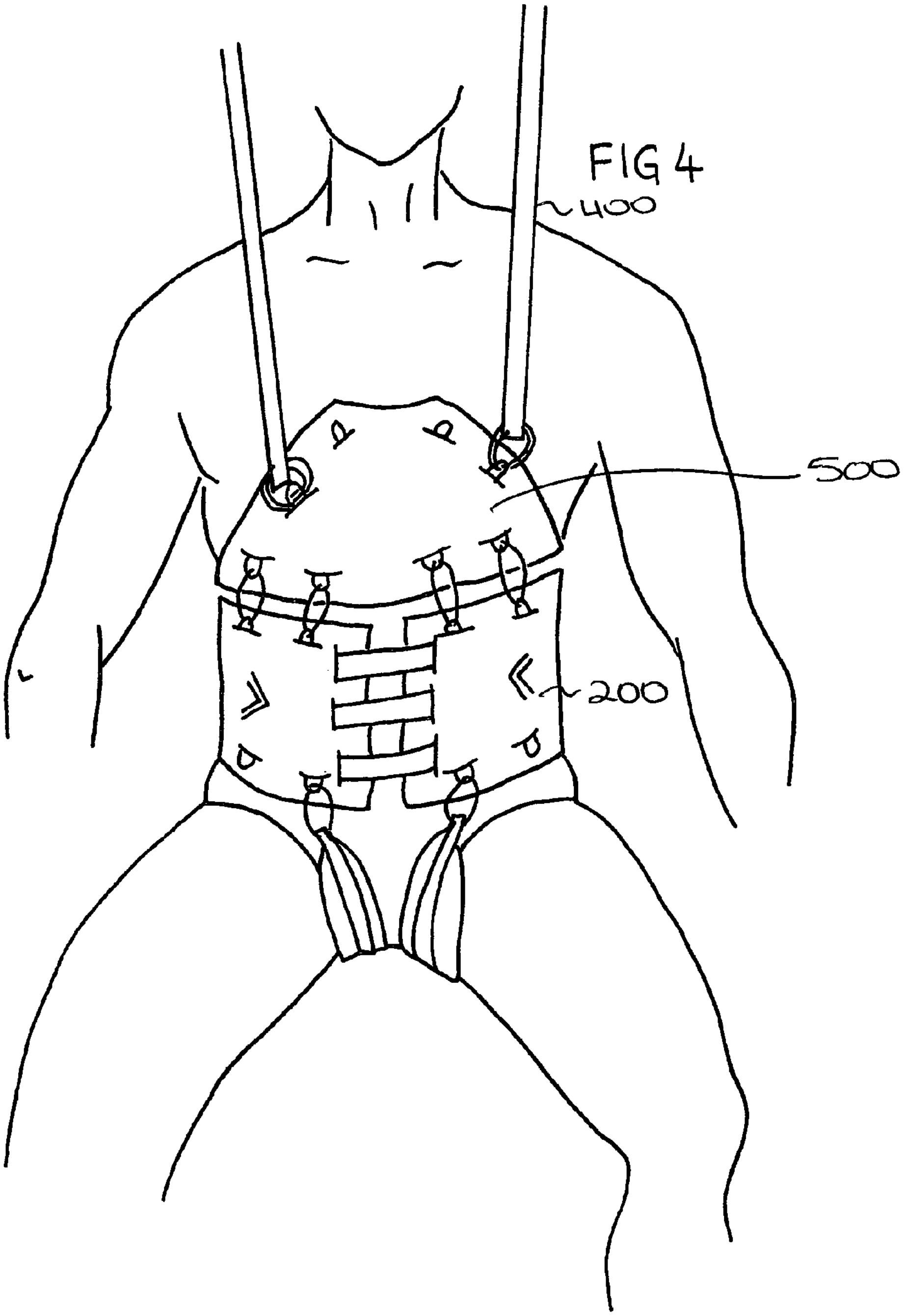
FIG. 4 shows an alternative positioning of the rib/chest pad 500 on the front of the patient.

FIG. 4 illustrates the same task as described above for FIG. 1, but the garment arrangement and assist straps attachment location is changed. The rib/chest pad, 500, is attached via the attachment means fixed to both the rib/chest pad and the pelvic belt to the pelvic belt in the front. This will provide additional support if a patient tends to fall forward, but could equally be used on one side or the other, or in the back.

Figure 5:
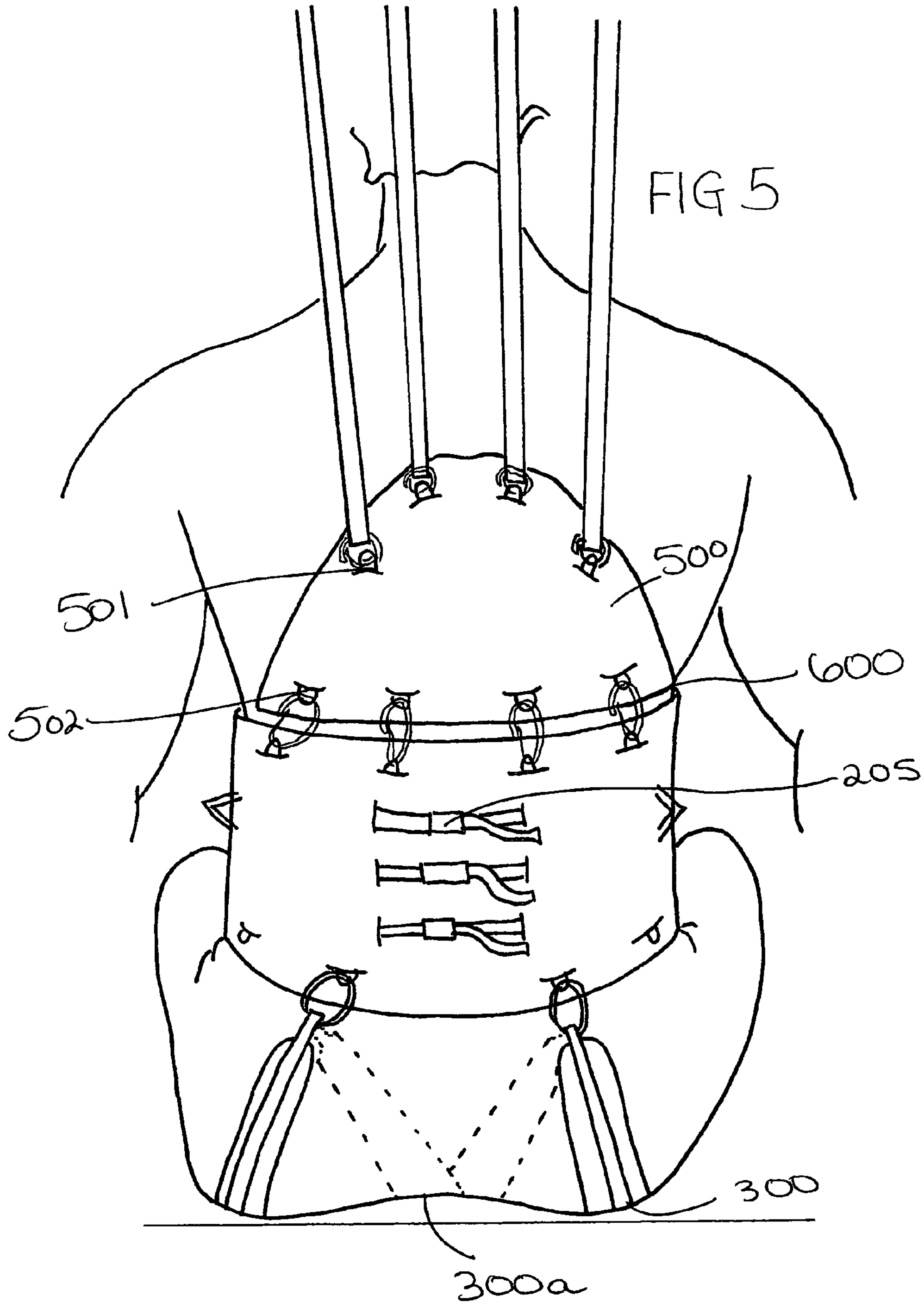
FIG. 5 shows positioning the rib/chest pad 500 on the back portion of a patient and attached to the pelvic belt 200.

FIG. 5 illustrates the attachment of the rib/chest pad, 500, to the pelvic belt in the back. This position could be used if a patient tended to fall backwards. If the patient progressed and needed less support, the therapist could choose to use only the pelvic strap which would show patient progress.

Figure 6:
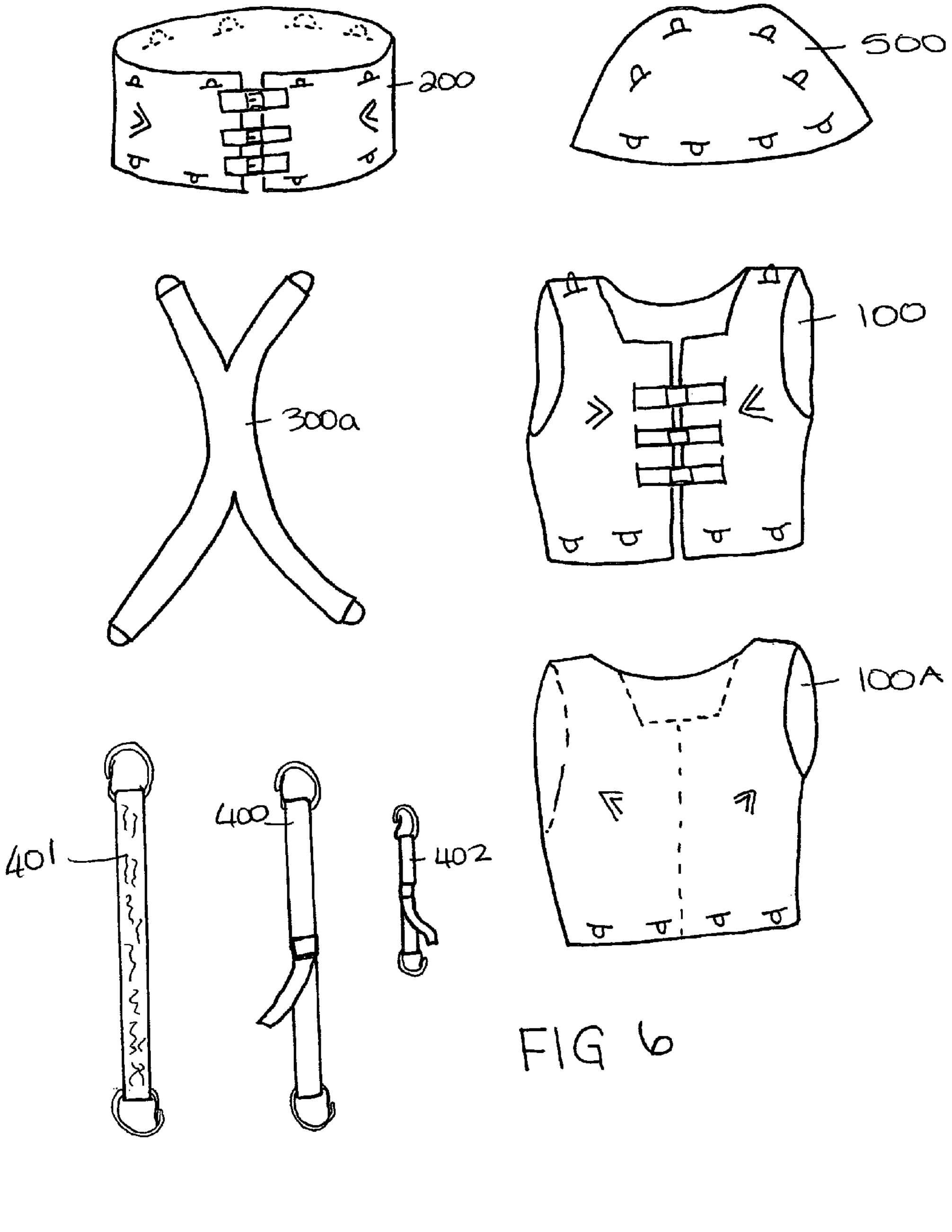
FIG. 6 illustrates the different pieces that may be assembled into a kit as supplied to hospitals and rehab locations.
Figure 6A:
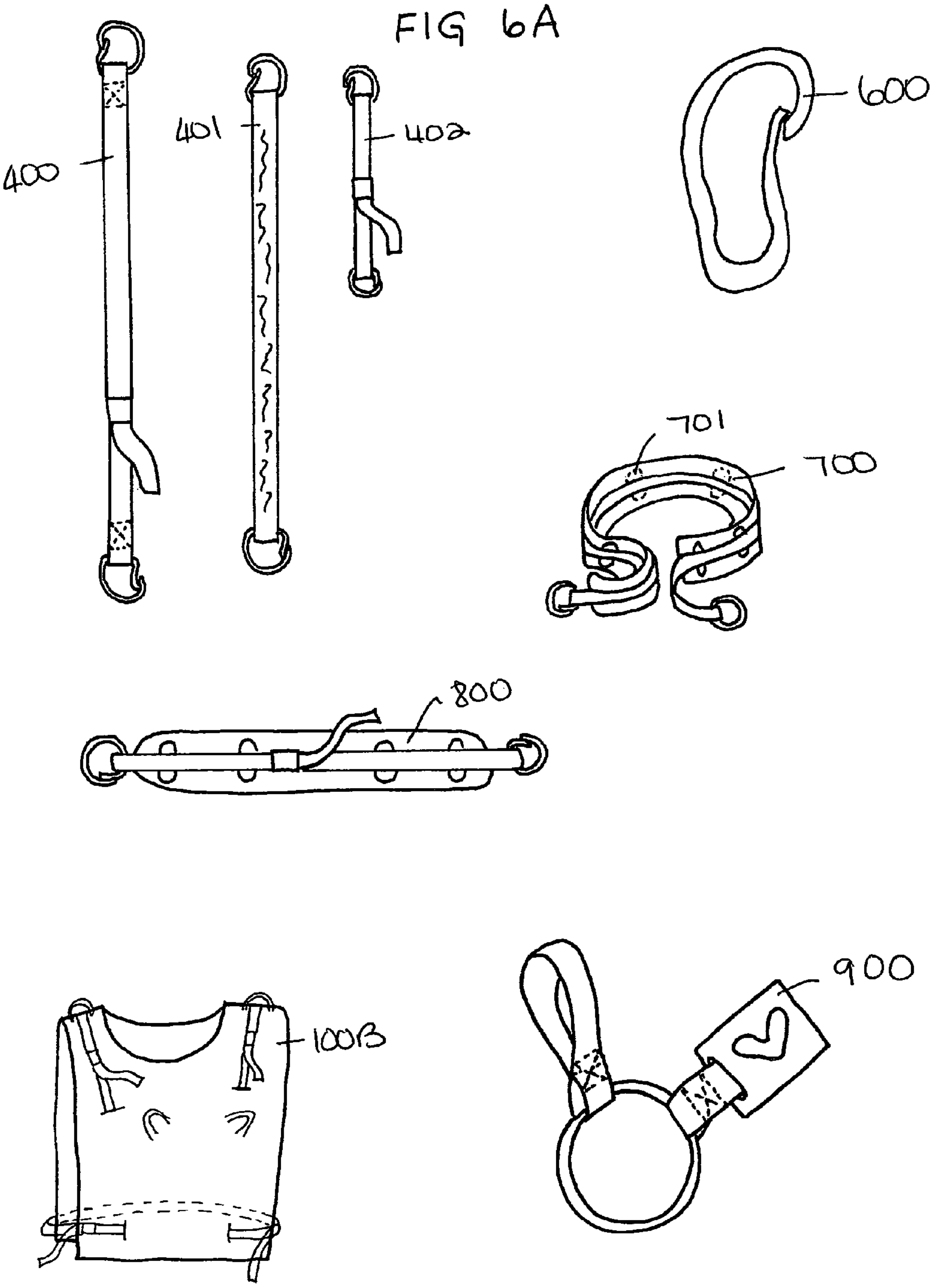
FIG. 6A illustrates another kit embodiment that includes other embodiments of the invention disclosed herein.

FIG. 6 shows one embodiment of a pre packaged kit that could be supplied to a caregiver giving her/him the flexibility to work with patients having different needs. Number 100A illustrate the back side of the vest 100. The kit contains for example the various pieces shown there. FIG. 6A shows a different embodiment of a kit. Number 100B is another embodiment of a vest design that could be used.

Figure 7:
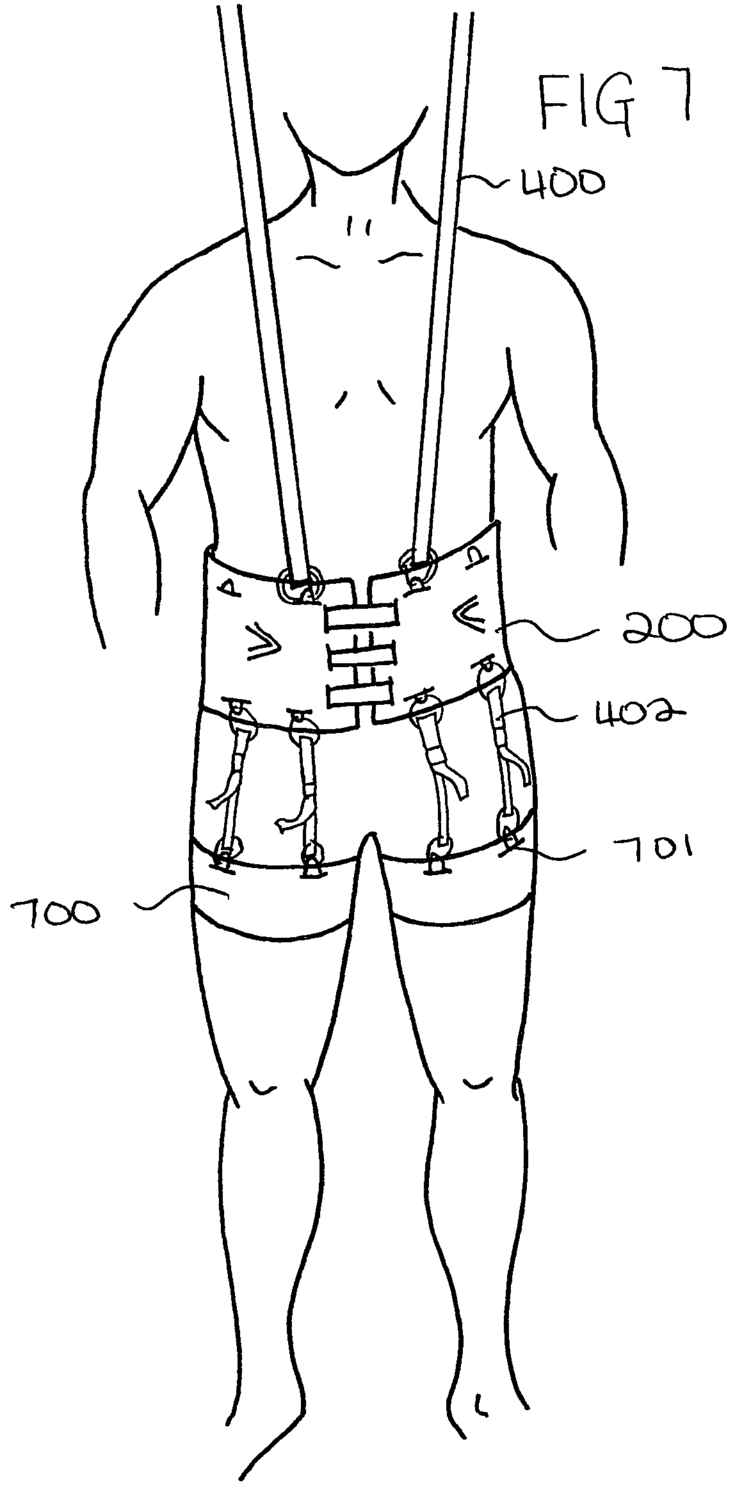
FIG. 7 is a front elevation showing the thigh supports 700 which are substituted for the crotch support shown in the previous FIG.s which are attached by webbing adjustable straps and wrapped around the thighs instead of under the crotch. This arrangement allows for the therapist to attach elastic strap (401) to front, back or side of the thigh to assist or resist advancement of the leg. It can also be used if straps in the crotch area are too uncomfortable.

FIG. 7 shows variation for leg support. The crotch strap, 300, is replaced with thigh supports 700 that securely tighten around a person thigh and are attached to the pelvic belt by straps 702. Occasionally, a patient needs to be ambulated when they still have a catheter in. In this case, the crotch strap could be exchanged for the thigh supports, 700, which would connect by the loops along the upper border of the supports by straps 702.

Figure 8:
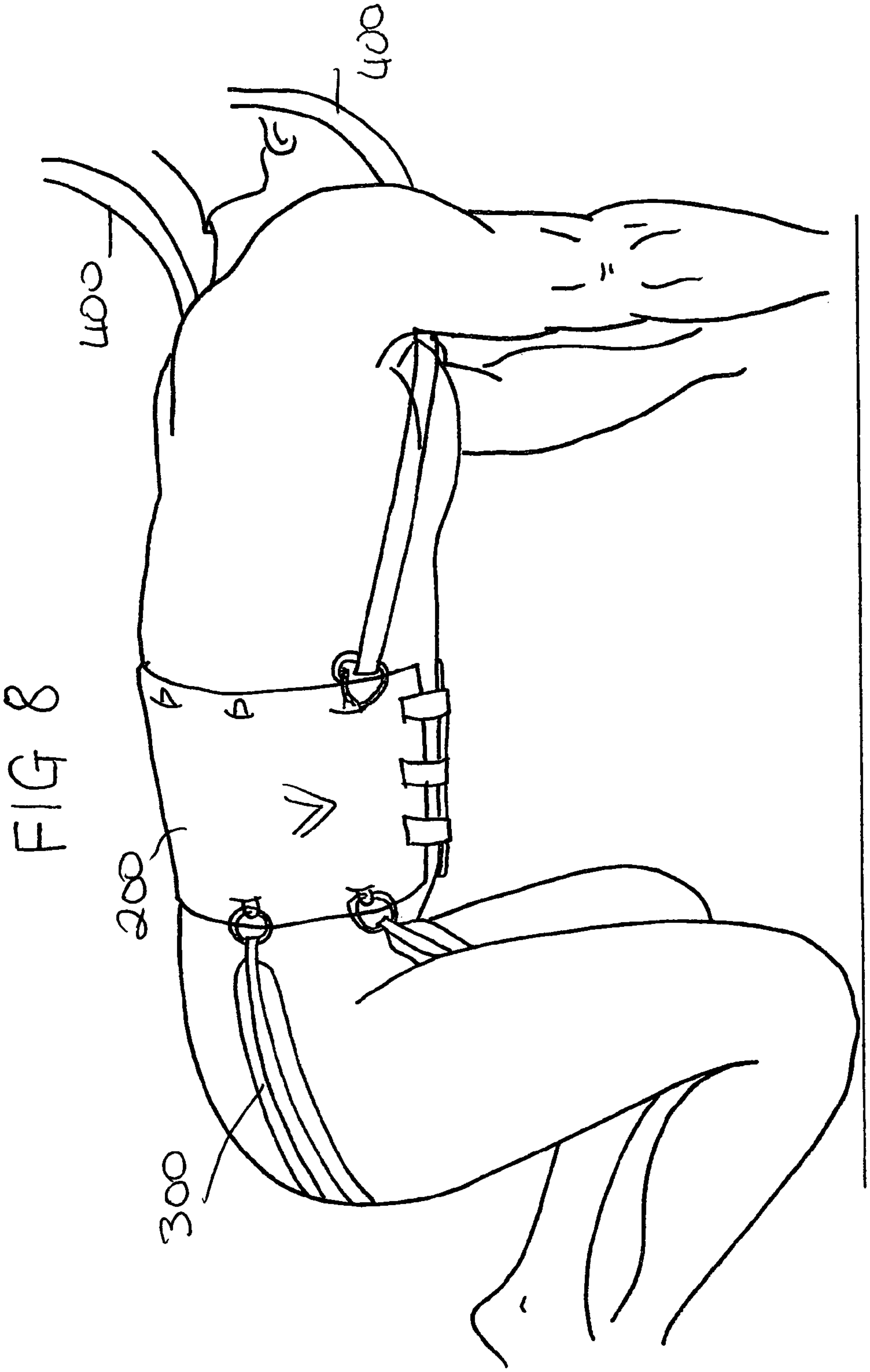
FIG. 8 is a view of a patient on hands and knees wearing just the pelvic belt and crotch support parts of the garment.
Figure 9:
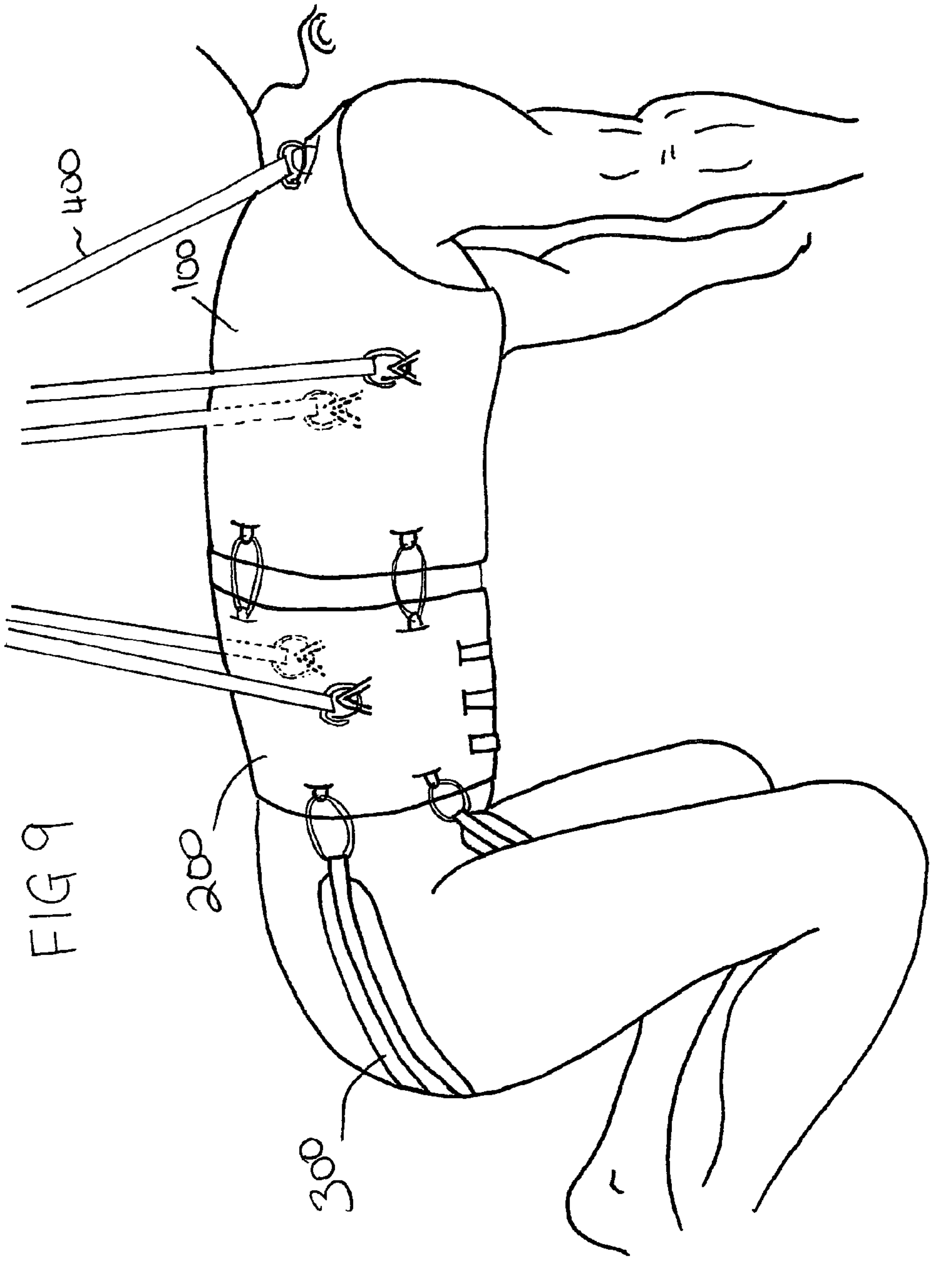
FIG. 9 is a view of a patient on hands and knees with the addition of the vest 100 for a patient who needs additional support in this position and assist straps 400 that can be attached to the pelvic belt and to the vest for maximum support.
Figure 9A:
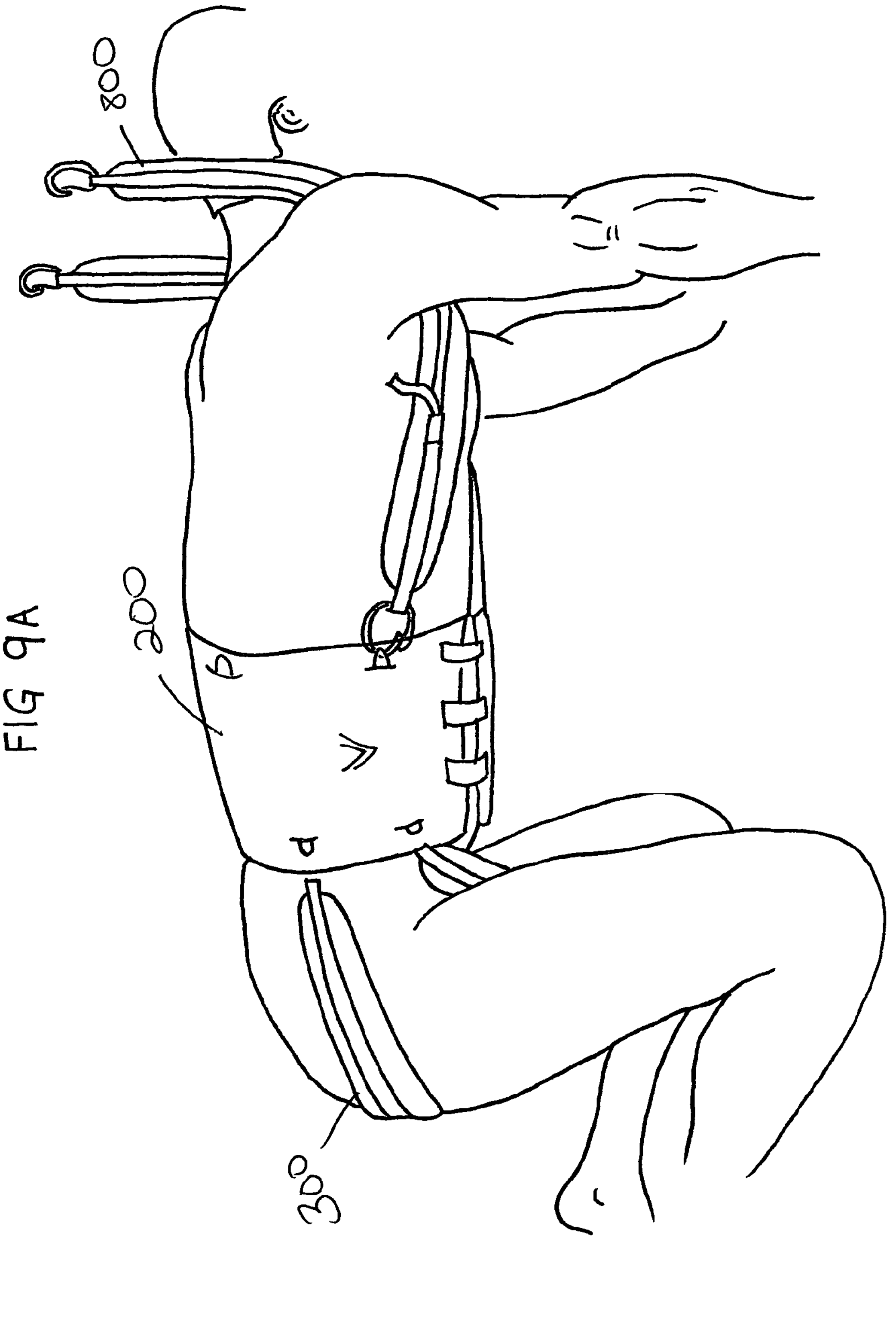
FIG. 9A shows a similar embodiment as FIG. 9 but using padded straps 800 instead of the vest 100.
Figure 10:
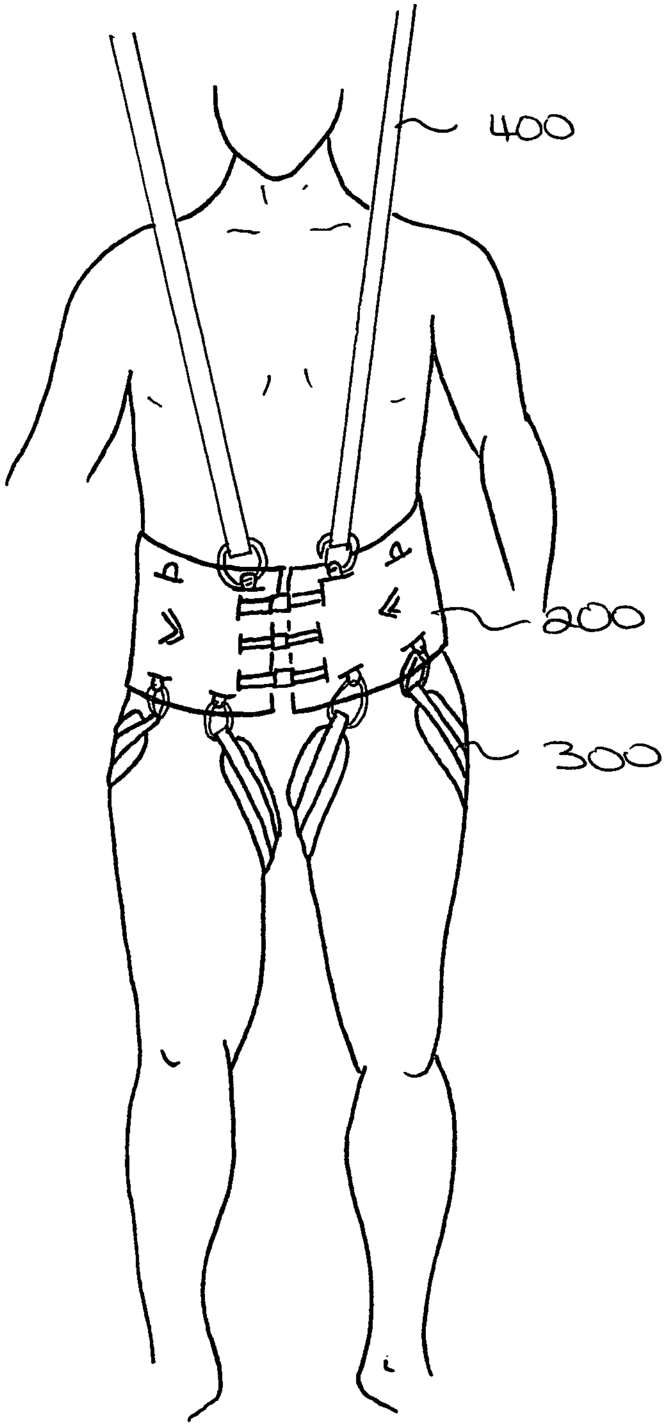
FIG. 10 is a front elevation of a patient wearing the pelvic belt and crotch support having two assist straps 400 attached to a different part of the pelvic belt.

FIG. 8 shows a patient on their hands and knees. This is an important developmental position for therapists to work on with patients, especially those who have had strokes or head injuries, where they need to re-learn movement similar to how a baby progresses from rolling to crawling to standing and walking. FIG. 8 shows only the pelvic belt, 200, the crotch support 300, and assist straps, 400, going forward along patients' torso in the front and up to a lift by the patients' shoulders. This would pull them upwards towards standing. FIG. 9 illustrates similar positional training but using in addition a vest to provide additional support. FIG. 9 A illustrates the use of the padded straps 800 instead of the vest 100.

Figure 11:
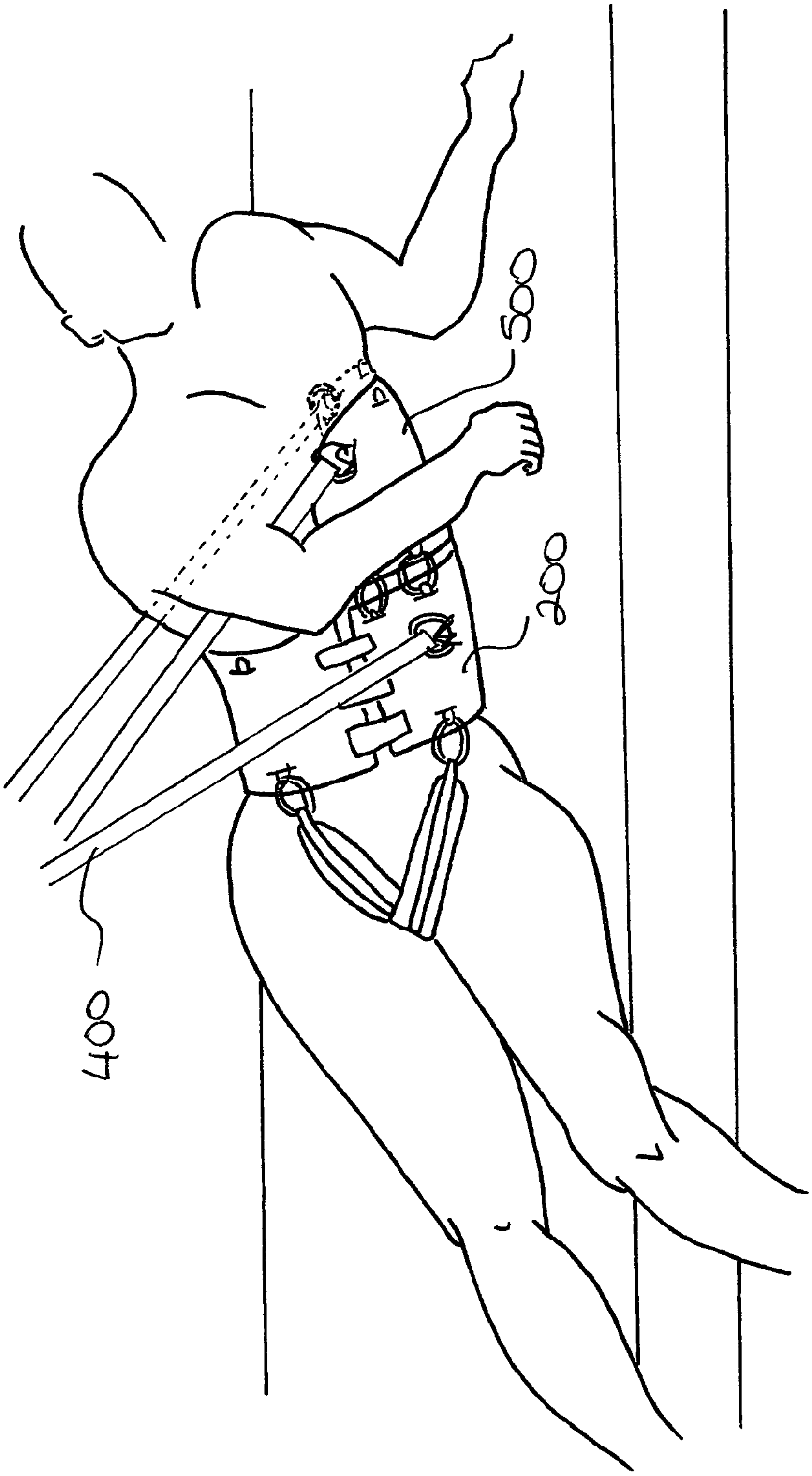
FIG. 11 is a side elevation view illustrating a patient being moved from a position, lying on their side, and coming up to a sitting position. This includes the pelvic belt, and rib/chest pad attached to the lower border of the pelvic belt by carabineer clips, the crotch strap and three assist straps, 400, two attached to the rib/chest pad via an attachment loop and one to the pelvic belt via one of the attachment loops fixed to the belt. In this application, with the higher back on piece 500, the rib/chest pad will facilitate more support to extend to the shoulder blade of the patient, if the extra support was needed.
Figure 11A:
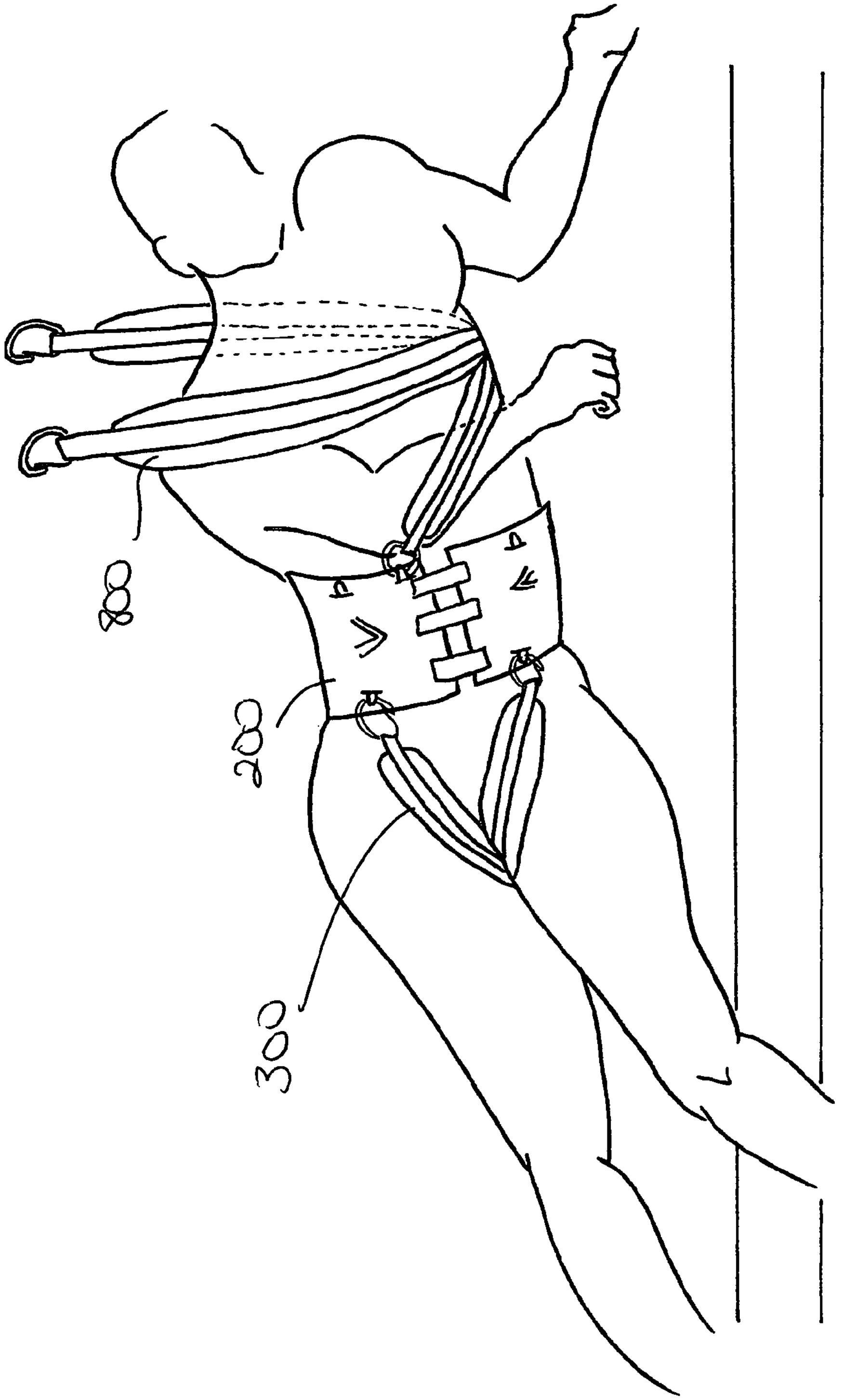
FIG. 11A is an alternative configuration to achieve side lying to sitting, as per FIG. 11 however the rib/chest pad, 500, is substituted with long padded straps, 800, that are crossed under the patients' ribs, to assist in bringing the patient up to a sitting position.
Figure 11B:
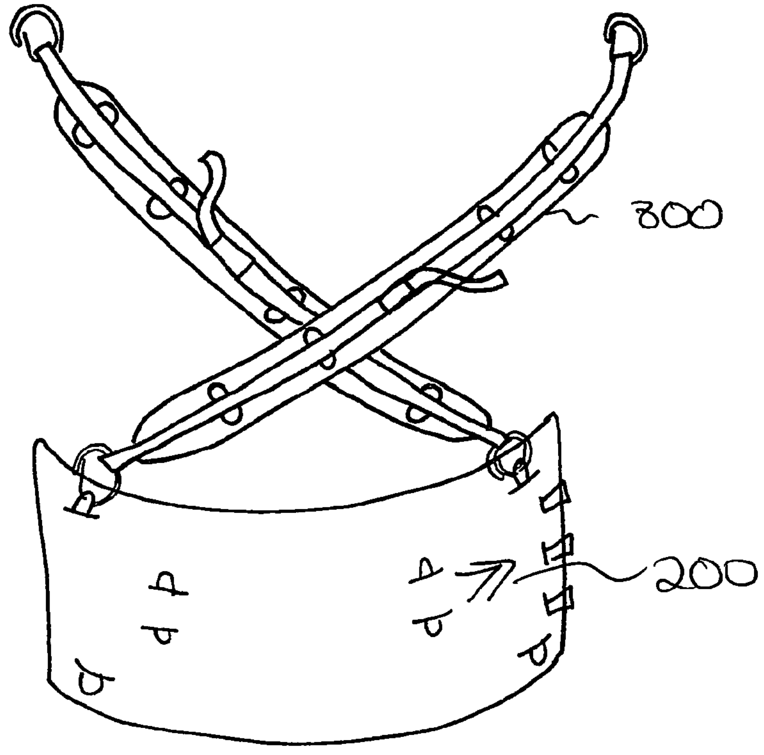
FIG. 11B shows the lateral view of just the pelvic belt 200 and the padded straps 800, without the patient, showing the crossing of the straps. They could be connected together in the crossed position back with a carabineer for example, if necessary to hold the cross in the desired location.

FIGS. 11 and 11A (11B illustrates the back view of just the pelvic belt 200 and long straps 800 show one of the most difficult manual tasks for therapists to perform, i.e., lifting a patient from a side lying position to a sitting position with legs extending over the edge of a bed. The therapist must lift both the torso, from under the patients' rib cage, as well as carefully lowering the legs over the side of the bed. The therapist is therefore at full stretch, in a bent over position, lifting at the same time. This is particularly unsafe for therapists to perform, Through use of the combination of the pelvic belt, 200, rib/chest pad, 500, or torso straps, 800, thigh/crotch straps, 300 and assist straps, 400 attached at even a different location on the pelvic garment; the desired angle of pull and desired level of support can be achieved. This is a particularly useful position for therapists to use to strengthen a patient's core muscles to help them be able to perform this task by themselves. By attaching elastic straps, 401 instead of rigid straps, 400, the patient can repeat the motion: Sit→lay→sit→lay→sit→lay, several times in one session, without harm or excessive fatigue of the therapist. Stronger elastic (more assistive, less "give") will make it easier for the patient, while weaker elastic straps (less assistive, more "give") will make it more difficult for the patient.

Figure 12:
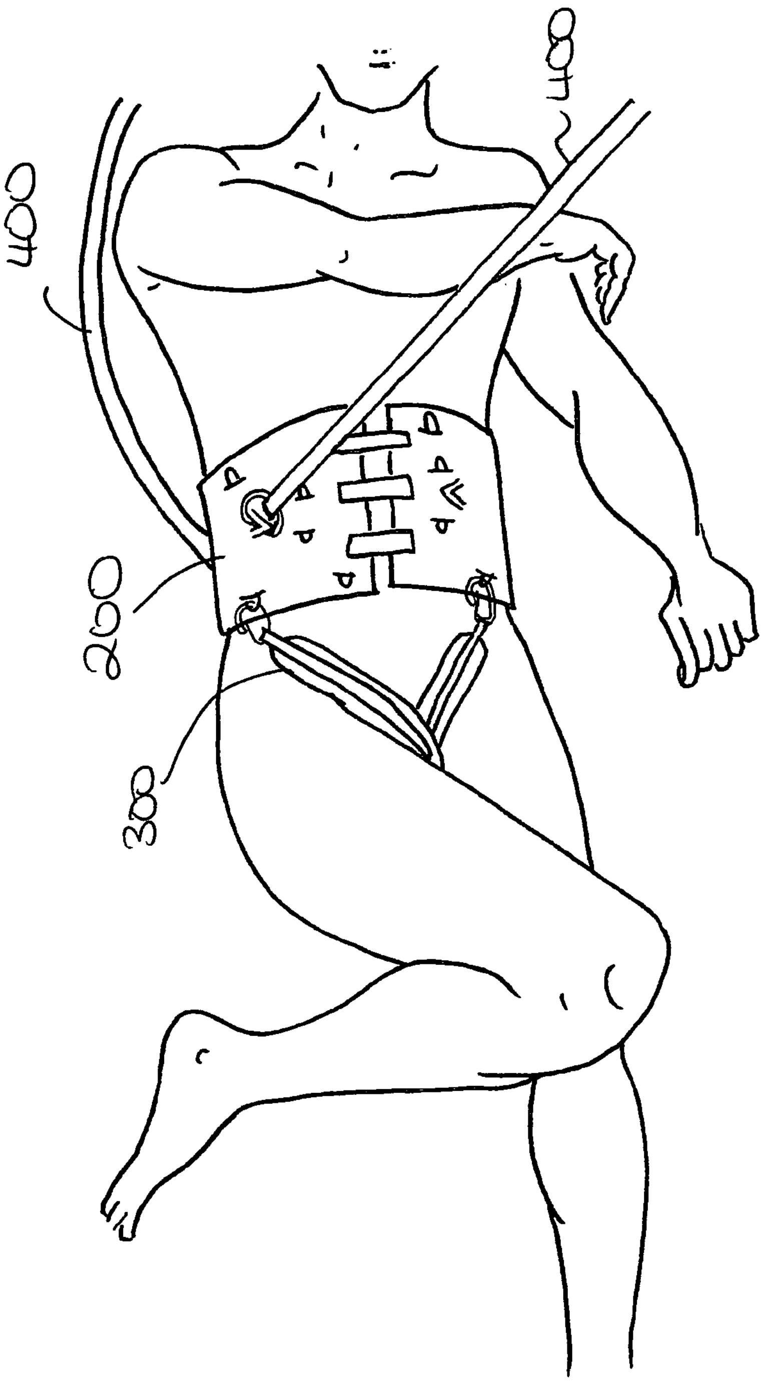
FIG. 12 shows an aerial view of a patient rolling over in bed. This shows the pelvic belt with an attached crotch strap using two assist straps, 400.

FIG. 12 Shows a patient being assisted from a position of lying on their backs to lying on their sides. This is a very difficult task to assist a patient doing because the caregiver or therapist must lean over the patient, and reach across the patients' body to pull the hips towards them. The mobility garment will allow the caregiver to either use better body mechanics pulling manually, by providing "Handles" to hold onto, or powered assistance using a device to pull.

Figure 13C:
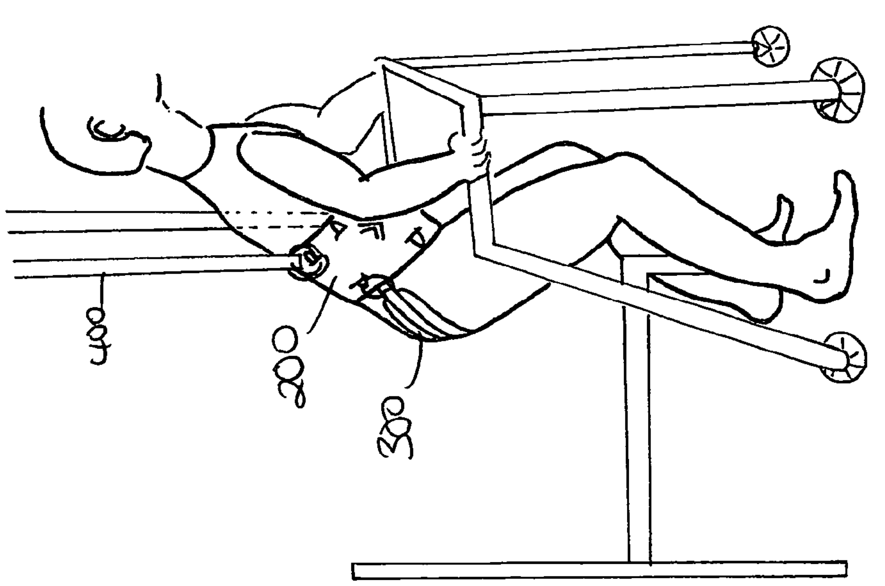
FIGS. 13A, 13B and 13C illustrate three examples of the use of the pelvic belt and the crotch/thigh supports, 300 and the use of two assist straps 400, attached to the pelvic belt via attachment means e.g. loops fixed to the belt for an alternative way of standing from sitting, using an overhead lift device as opposed to a floor-based sit-stand device.
Figure 13B:
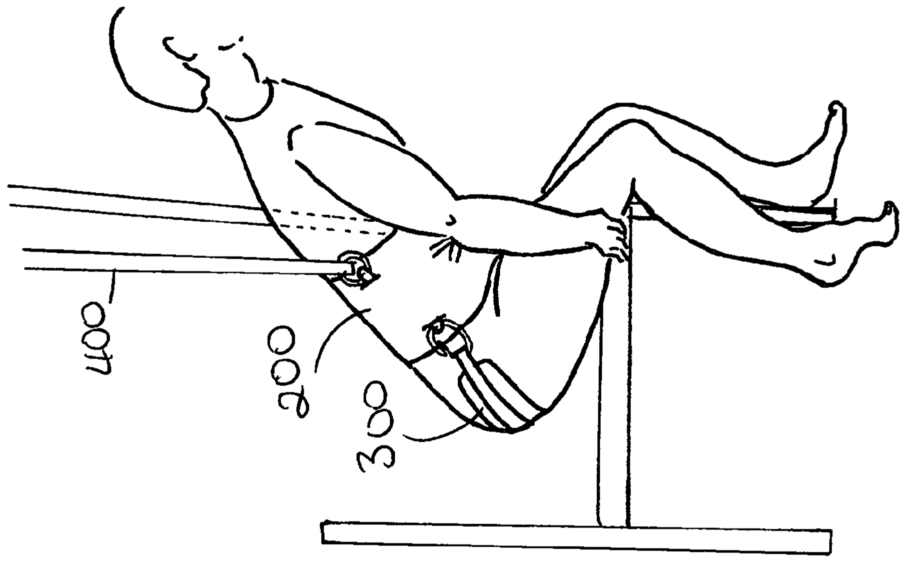
Figure 13A:
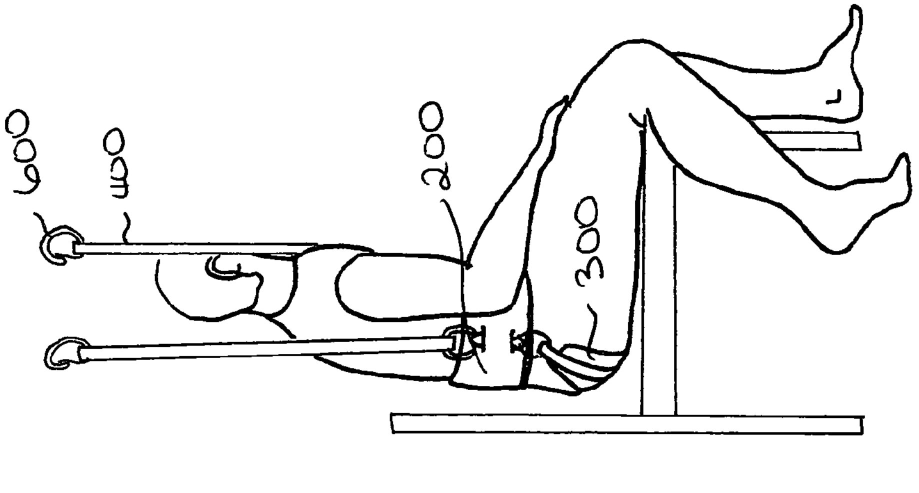

FIGS. 13A, B & C show a different application of the invention. By moving the assist straps 400 from the posterior loops to those on the anterior surface, and by changing the angle of pull improves the mobility of the patient. Some power-assist sit-stand devices have attachments that pull the patient forwards from the waist level. One problem with this approach is that the slings ride up under the patients' arms as they are pulled to stand. Attachment of the thigh/crotch strap, 300, prevents this from happening. In this application, the straps pull forwards. This is useful if the facility does not own or have access to the sit-stand lifts, or if the therapist wants the patient to do more for themselves. In this case, the straps, 400, are moved to the webbing loops along the upper border of the pelvic belt, and the force is pulled straight upwards. The patient can then use a walker or other assistive device if necessary, and instead of the therapist having to physically hold the patient up, they can focus on correct movement for the patient.

Figure 14:
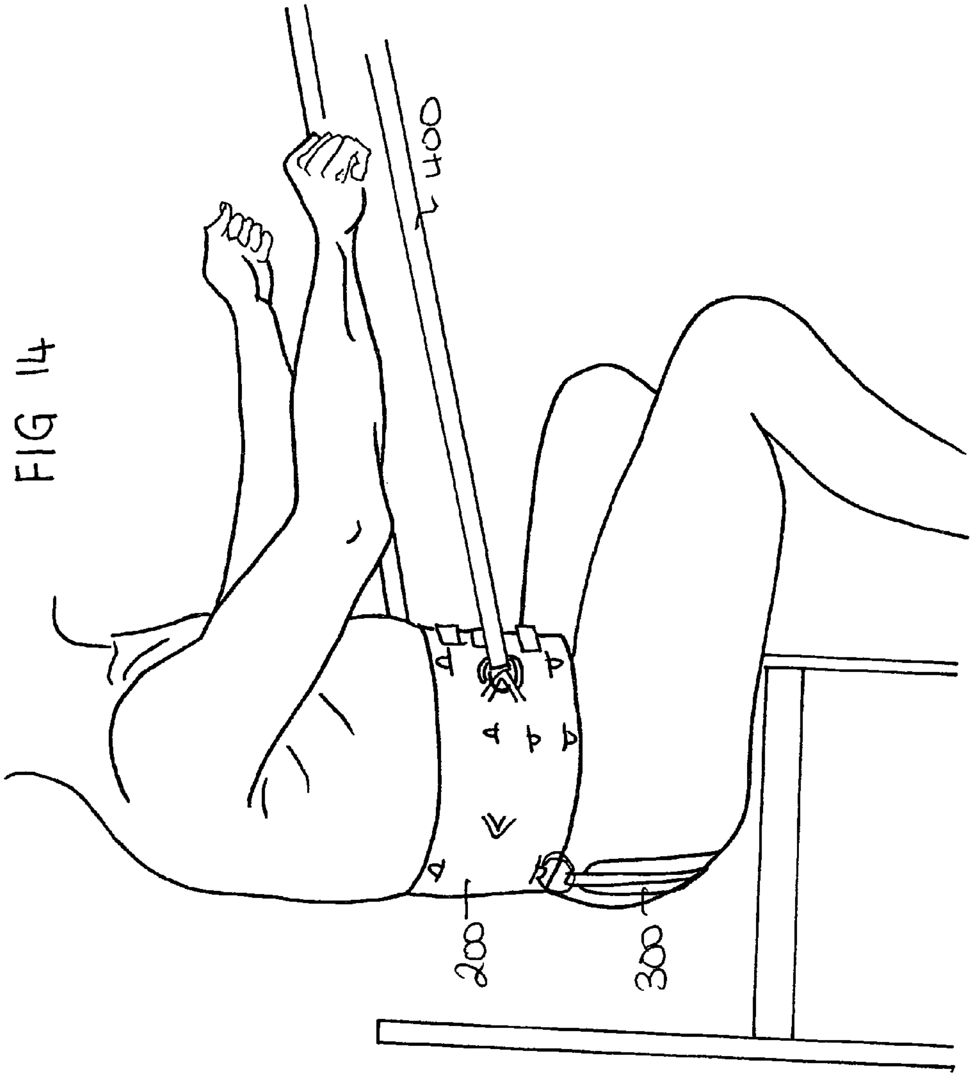
FIG. 14 is view of a patient in a sitting position and wearing the pelvic belt and crotch support pieces of the garment. In this position, the patient is sitting and preparing to stand. Two assist straps, 400 are attached to loops located on the front of the pelvic belt and to a mechanical lifting device, not shown, to assist the patient in coming to a standing position.

FIG. 14 shows a hook up for assistance with sitting to standing. In this case, the device that assists the patient is usually in front of them, and the patient needs assistance getting their weight forward. Simple change in location of attachment will accomplish this without having to switch the sling or garment.

Figure 15:
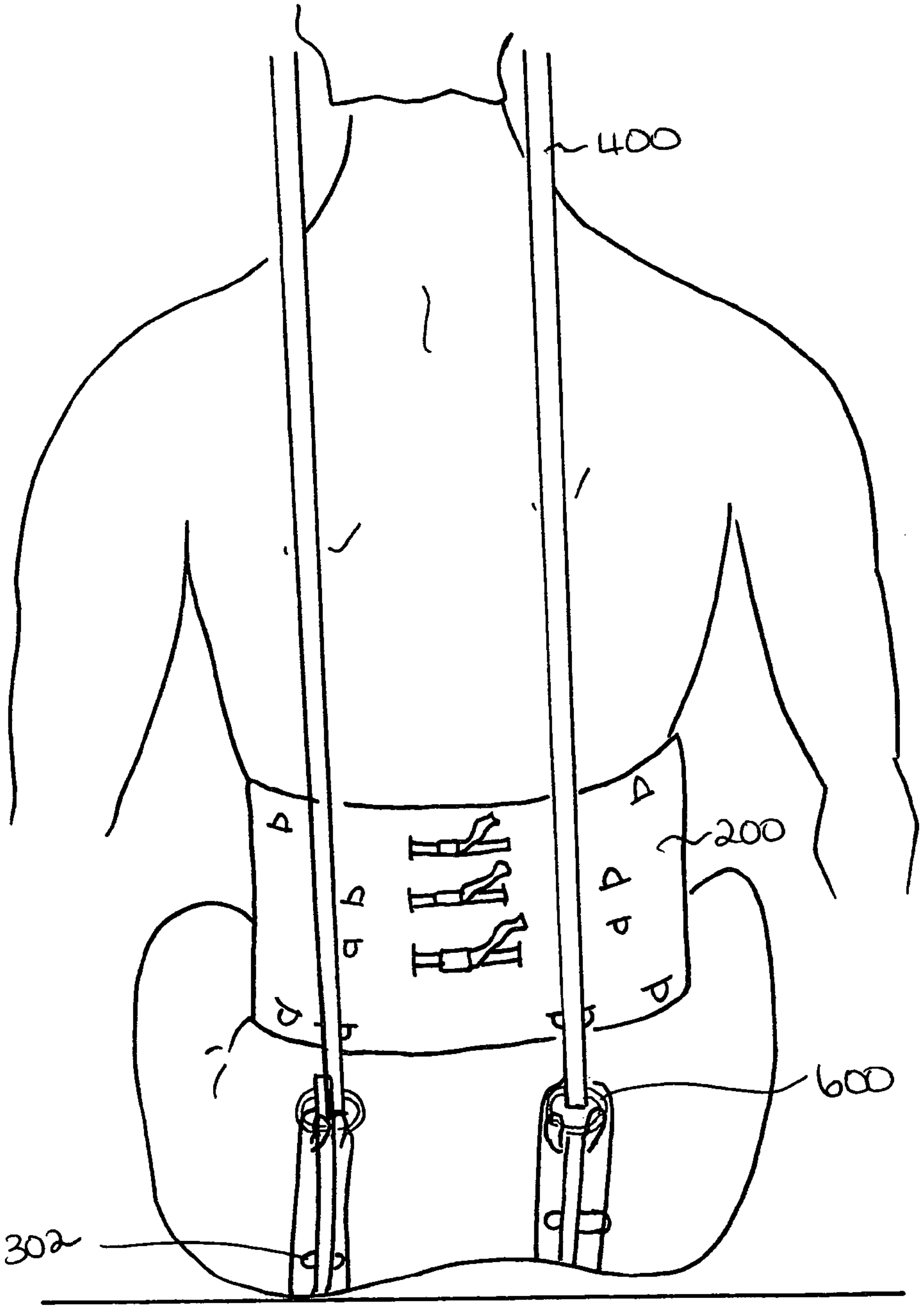
FIG. 15 is an alternative configuration of attachments where the assist straps are affixed to attachment means, loops or D rings for example fixed to the thigh/crotch straps directly. This lower attachment point will be more helpful in assisting a patient to lift their buttocks off a chair, for example, in chair-chair transfers, or wheelchair to bed transfers where the back of the buttocks need to clear the edge of the bed for example. The attachment straps, 400, would connect to a ceiling based or dependent lift with the frame overhead.
Figure 16:
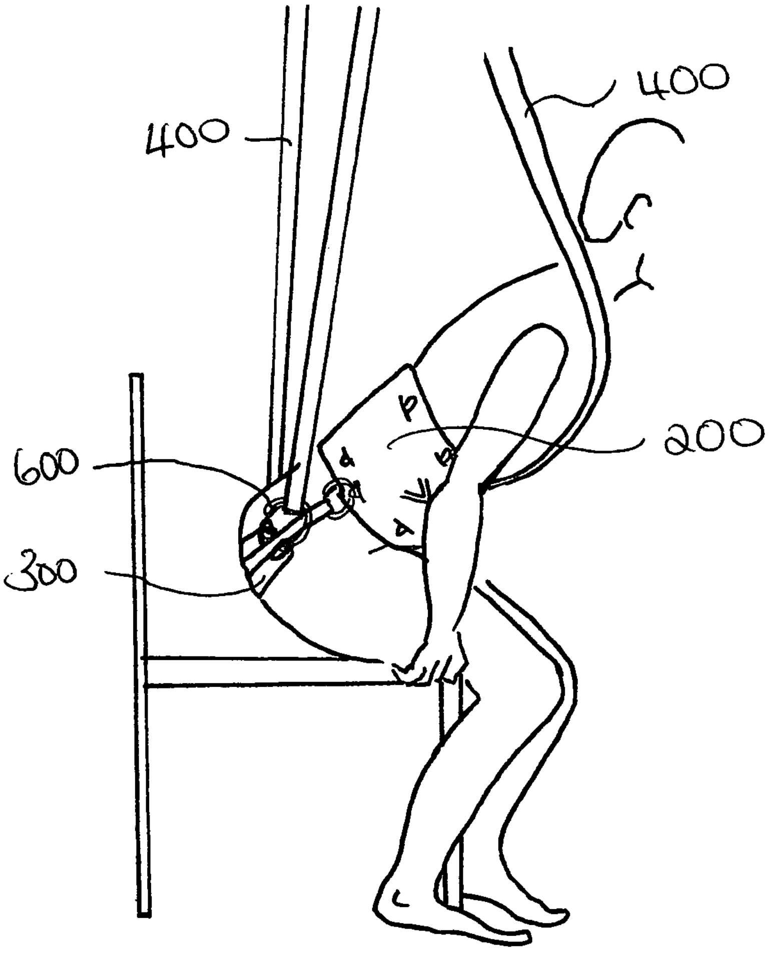
FIG. 16 shows how attachment position of the assist straps shown in FIG. 15 can be used to pull the patient up. Additionally, another attachment strap, 400 or a long padded torso/shoulder strap 800, could be used in front of the patient if they were fearful or at risk of falling forward.

FIGS. 14, 15 and 16 illustrate different assist strap hook up locations on a patient wearing a pelvic belt and thigh/crotch support 300. One very difficult task caretaker task is chair to chair transfer of a patient. For example, a patient who has had a spinal cord injury and has no strength in their legs will need special assistance. Lifting their trunk up to assist with this transfer, as they work on strengthening their arms up to perform the task independently is a very difficult task for the therapist and puts them at significant risk of injury. This application of the invention permits the use of a mechanical lift device to support some of the patient weight, from the right place, and allow the therapist to work with the patient on the arm strength portion of the task. If the attachment were to the top of the pelvic belt, as is the case in most prior art and slings currently available, the vertical force would only pull up the patients' torso, and would not achieve the up and forward motion required for successful transfer. Current art and garments do not easily allow this activity.

The central concept of this invention is the variability and versatility of the combinations of pieces and assists straps that can be used in many positions and mobility tasks to help the therapists provide the most progressive care that the patient can tolerate without causing harm or injury to the therapist or caregiver.

It will now be evident to those skilled in the art the invention described herein provides an improved lifting assistance garment. The description of the present invention has been presented for illustration and description, and is not intended to be exhaustive or limited to the invention in the form disclosed. Many modifications and variations will be apparent to those of ordinary skill in the art. The embodiments were chosen and described to best explain the principles of the invention, the practical application, and to enable others of ordinary skill in the art to understand the invention for various embodiments with various modifications as suited to the use contemplated.

Although the invention has been described by way of preferred embodiments, it will be evident that other adaptations and modifications can be employed without departing from the spirit and scope thereof. While the depicted embodiment shows the multiple assist straps attached to the outer-facing surface of the garment member, it is within the scope of the invention that the straps may be incorporated into the composite construction of the material forming the garment member. The terms and expressions employed have been used as terms of description and not of limitation; and there is no intent of excluding equivalents, but on the contrary it should cover any and all equivalents that may be employed without departing from the spirit and scope of the invention.

What is claimed is:

1. A patient assistance garment for assisting a human patient having a torso, a rib cage, a waist, hips, and an armpit, which is configured to be worn on the torso of the patient, and which provides assistance to a caregiver assisting the patient comprising:

a pelvic belt having a surface, and a width and a length configured to fit around the waist of the patient below the rib cage and above the hips, the length having an open front that contains at least one adjustable strap and buckle combination to secure the garment around the torso; a top rim; and a bottom rim;

multiple attachment means fixed to the pelvic belt along the top rim and the bottom rim for attaching and detaching other garments to the pelvic belt through attachment with corresponding attachment means fixed to the other garments; and additional attachment means fixed to the surface of the pelvic belt along the length and located below the attachment means fixed along the top rim and above the attachment means fixed along the bottom rim of the pelvic belt, the additional attachment means functioning to attach and detach assist straps to the pelvic belt;

wherein at least one of the following pieces is present in addition;

a pair of thigh/crotch straps, which are attachable and detachable to the attachment means fixed along the bottom rim of the pelvic belt, and which also have a plurality of attachment means lengthwise along a middle of the thigh/crotch straps for attachment and detachment of assist straps;

a pair of long padded straps, which contain multiple attachment means for attaching and detaching the pair of long padded straps to and from the attachment means and the additional attachment means of the pelvic belt;

multiple assist support straps, which are either rigid or elastic, each of which includes attachment means at a first end of the assist support strap for attaching the assist support strap to the attachment means and the additional attachment means of the pelvic belt, and attachment means at a second end for connecting the assist support strap to a lift apparatus;

a rib/chest pad, which has a rib/chest pad lower rim that approximates about one half the length at the top rim of the pelvic belt: two sides that taper to fit below the armpit of the patient; and, on an outer surface of the rib/chest pad, not only attachment means located along the he rib/chest pad lower rim for attaching the rib/chest pad to the attachment means located along the ton rim of the pelvic belt but also additional attachment means for attaching assist straps to the rib/chest pad; and an open front vest, which has a vest front, a vest surface, vest shoulders, a neck edge, a lower edge, a vest waist edge, a vest armpit, and chest areas including a center; multiple adjustable length web strap/buckle combinations attached to the vest front to close the vest front; multiple attachment means attached to the vest surface, first attachment means being attached to each vest shoulder, and second attachment means being on each chest area midway between the neck edge and the waist edge, and midway between the center and the vest armpit; and multiple attachment means attached along the lower edge of the open front vest for attachment and detachment to the attachment means located along the top rim of the pelvic belt.

2. The garment of claim 1, wherein the pelvic belt includes a back outer surface and a side outer surface; and the garment includes in addition at least one adjustable strap and buckle combination attached to at least one of the back outer surface and the side outer surface of the pelvic belt, which can be adjusted to gather material of the pelvic belt and further adjust the length of the pelvic belt.

3. The garment of claim 1, which includes the pair of thigh/crotch straps.

4. The garment of claim 1, which includes the pair of long padded straps.

5. The garment of claim 1, which includes the multiple assist support straps.

6. The garment of claim 1, which includes the rib/chest pad.

7. The garment of claim 6, wherein the rib/chest pad is in a form of a semi-circle.

8. The garment of claim 1, which includes the open front vest.

9. The garment of claim 1, wherein the attachment means and the additional attachment means include loops.

10. A patient assistance garment for assisting a human patient having a torso, a rib cage, a waist, hips, and an armpit, which is configured to be worn on the torso of the patient, and which provides assistance to a caregiver assisting the patient, comprising:

a pelvic belt having a surface, and a width and a length configured to fit around the waist of the patient below the rib cage and above the hips, the length having an open front that contains at least one adjustable strap and buckle combination to secure the garment around the torso; a top rim; and a bottom rim;

multiple attachment means fixed to the surface of the pelvic belt along the top rim and the bottom rim for attaching and detaching other garments to the pelvic belt;

additional attachment means fixed to the surface of the pelvic belt along the length and located below the attachment means fixed along the top rim and above the attachment means fixed along the bottom rim of the pelvic belt, the additional attachment means functioning to attach and detach assist straps to the pelvic belt; and a pair of thigh/crotch straps, which are attachable and detachable to the attachment means fixed along the bottom rim of the pelvic belt, and which also have a plurality of attachment means lengthwise along a middle of the thigh/crotch straps for attachment and detachment of assist straps.

11. The garment of claim 10, which includes in addition at least one adjustable strap and buckle combination attached to at least one of a back outer surface and a side outer surface of the pelvic belt, which can be adjusted to gather material of the pelvic belt and further adjust the length of the pelvic belt.

12. The garment of claim 10, which includes in addition a pair of long padded straps that contain multiple attachment means for attaching and detaching assist straps to the long padded straps, the long padded straps including attachment means for attaching and detaching the long padded straps from the attachment means and the additional attachment means of the pelvic belt.

13. The garment of claim 10, which includes in addition multiple assist support straps that are either rigid or elastic, and that include attachment means at a first end of each multiple assist strap for attaching the assist support strap to the pelvic belt, and at a second end contains attachment means for connecting the assist support strap to a lift apparatus.

14. The garment of claim 10, which includes in addition a rib/chest pad that has a lower rim that approximates about one half the length at the top rim of the pelvic belt, two sides that taper to fit below the armpit of the patient, and, on an outer surface of the rib/chest pad, not only attachment means located along the rib/chest pad lower rim for attaching the rib/chest pad to the attachment means located along the top rim of said pelvic belt but also additional attachment means for attaching assist straps to the rib/chest pad.

15. The garment of claim 14, wherein the rib/chest pad is in a form of a semi-circle.

16. The garment of claim 10, which includes in addition an open front vest having a vest front, a vest surface, vest shoulders, a neck edge, a lower edge, a vest waist edge, a vest armpit, and chest areas including a center; multiple adjustable length web strap/buckle combinations attached to the vest front to close the vest front; multiple attachment means attached to the vest surface, first attachment means being attached to each vest shoulder, and second attachment means being on each chest area midway between the neck edge and the vest waist edge, and midway between the center and the vest armpit; and multiple attachment means attached along the lower edge of the open front vest for attaching the open front vest to the attachment means located along the top rim of the pelvic belt.

17. The garment of claim 10, wherein the attachment means and the additional attachment means include loops.

* * * * *